United States Patent
Hayter

(10) Patent No.: US 10,028,686 B2
(45) Date of Patent: *Jul. 24, 2018

(54) METHODS FOR GENERATING HYBRID ANALYTE LEVEL OUTPUT, AND DEVICES AND SYSTEMS RELATED THERETO

(71) Applicant: Abbott Diabetes Care Inc., Alameda, CA (US)

(72) Inventor: Gary A. Hayter, Oakland, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 141 days.

This patent is subject to a terminal disclaimer.

(21) Appl. No.: 15/077,520

(22) Filed: Mar. 22, 2016

(65) Prior Publication Data

US 2016/0262669 A1 Sep. 15, 2016

Related U.S. Application Data

(63) Continuation of application No. 13/538,406, filed on Jun. 29, 2012, now Pat. No. 9,289,164.

(60) Provisional application No. 61/503,338, filed on Jun. 30, 2011.

(51) Int. Cl.
| | |
|---|---|
| *A61B 5/00* | (2006.01) |
| *A61B 5/1495* | (2006.01) |
| *A61B 5/145* | (2006.01) |

(52) U.S. Cl.
CPC ........ *A61B 5/1495* (2013.01); *A61B 5/14532* (2013.01)

(58) Field of Classification Search
None
See application file for complete search history.

(56) References Cited

U.S. PATENT DOCUMENTS

| | | |
|---|---|---|
| 4,545,382 A | 10/1985 | Higgins et al. |
| 4,686,825 A | 8/1987 | Cavasa et al. |
| 4,711,245 A | 12/1987 | Higgins et al. |
| 5,262,035 A | 11/1993 | Gregg et al. |
| 5,262,305 A | 11/1993 | Heller et al. |
| 5,264,014 A | 11/1993 | Lannefors et al. |
| 5,264,104 A | 11/1993 | Gregg et al. |
| 5,320,715 A | 6/1994 | Berg |
| 5,356,786 A | 10/1994 | Heller et al. |
| 5,509,410 A | 4/1996 | Hill et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 6,071,391 A | 6/2000 | Gotoh et al. |
| 6,120,676 A | 9/2000 | Heller et al. |
| 6,121,009 A | 9/2000 | Heller et al. |
| 6,143,164 A | 11/2000 | Heller et al. |

(Continued)

*Primary Examiner* — Michael R Bloch
(74) *Attorney, Agent, or Firm* — Vorys, Sater, Seymour and Pease LLP

(57) ABSTRACT

Generally, methods, devices, and systems for generating a hybrid analyte level output are provided. The uncompensated analyte levels lag in time with respect to the lag-compensated analyte levels, and the hybrid analyte level output tracks between the uncompensated analyte levels and the lag-compensated analyte levels according to predetermined criteria.

20 Claims, 12 Drawing Sheets

(56) References Cited

U.S. PATENT DOCUMENTS

| | | |
|---|---|---|
| 6,144,837 A | 11/2000 | Quy |
| 6,161,095 A | 12/2000 | Brown |
| 6,175,752 B1 | 1/2001 | Say et al. |
| 6,284,478 B1 | 4/2001 | Heller et al. |
| 6,270,455 B1 | 8/2001 | Brown |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,650,471 B2 | 11/2003 | Doi |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,942,518 B2 | 9/2005 | Liamos et al. |
| 7,041,468 B2 | 5/2006 | Drucker et al. |
| 7,167,818 B2 | 1/2007 | Brown |
| 7,299,082 B2 | 11/2007 | Feldman et al. |
| 7,811,231 B2 | 10/2010 | Jin et al. |
| 2004/0186365 A1 | 9/2004 | Jin et al. |
| 2006/0025662 A1 | 2/2006 | Buse et al. |
| 2006/0091006 A1 | 5/2006 | Wang et al. |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0199818 A1 | 8/2007 | Petyt et al. |
| 2008/0066305 A1 | 3/2008 | Wang et al. |
| 2008/0081977 A1 | 4/2008 | Hayter et al. |
| 2008/0102441 A1 | 5/2008 | Chen et al. |
| 2008/0148873 A1 | 6/2008 | Wang |
| 2008/0267823 A1 | 10/2008 | Wang et al. |
| 2009/0198118 A1 | 8/2009 | Hayter et al. |
| 2009/0204341 A1* | 8/2009 | Brauker .............. A61B 5/1468 702/19 |
| 2010/0198034 A1 | 8/2010 | Thomas et al. |
| 2010/0325868 A1 | 12/2010 | Wang et al. |

* cited by examiner

METHODS FOR GENERATING HYBRID ANALYTE LEVEL OUTPUT, AND DEVICES AND SYSTEMS RELATED THERETO

CROSS-REFERENCE TO RELATED APPLICATION

This application is a continuation of U.S. patent application Ser. No. 13/538,406 filed Jun. 29, 2012, now U.S. Pat. No. 9,289,164, which application claims the benefit of priority under 35 U.S.C. § 119(e) to U.S. Provisional Patent Application No. 61/503,338 filed Jun. 30, 2011, the disclosures of which are incorporated by reference herein in their entirety.

BACKGROUND

In many instances it is desirable or necessary to regularly monitor the concentration of particular constituents in a fluid. A number of systems are available that analyze the constituents of bodily fluids such as blood, urine and saliva. Examples of such systems conveniently monitor the level of particular medically significant fluid constituents, such as, for example, cholesterol, ketones, vitamins, proteins, and various metabolites or blood sugars, such as glucose. Diagnosis and management of patients suffering from diabetes mellitus, a disorder of the pancreas where insufficient production of insulin prevents normal regulation of blood sugar levels, requires carefully monitoring of blood glucose levels on a daily basis.

In vivo analyte monitoring systems include an in vivo analyte sensor. At least a portion of the sensor is positioned beneath the skin surface of a user to contact bodily fluid (e.g., blood or interstitial fluid (ISF)) to monitor one or more analytes in the fluid over a period of time. This is also referred to as continuous analyte monitoring in that the sensor remains positioned in the user for a continuous period of time. Other forms of testing include in vitro testing—e.g., by withdrawing blood from a patient and applying the blood to a test strip for insertion into an analyte monitoring device, such as a glucose meter.

ISF glucose may lag in time behind blood glucose. That is, if the blood glucose is falling and reaches a low point, the ISF glucose will reach that low point some time later, such as 10 minutes for example. Traditionally, the goal of analyte monitoring systems is to provide results that approximate blood glucose concentrations since blood glucose concentrations may better represent the glucose level in the patient's blood.

SUMMARY

Aspects of the present disclosure relate to methods, devices and systems that generate a hybrid analyte level output including uncompensated analyte levels and lag-compensated analyte levels. The hybrid analyte level outputs may track the lag-compensated analyte levels at certain times, and track uncompensated analyte levels at other times. Various criteria (e.g., times, conditions, events, etc.) may be predetermined and associated with the tracking of lag-compensated analyte levels or the tracking of uncompensated analyte levels. For example, there may be times when a lag-compensated signal is more important, such as during high and/or low analyte level reading, or when high rates-of-change occur in the analyte levels, etc. Lag-compensation may generally improve accuracy during high rates-of-change, for instance, because the lag-compensated signal will respond faster than the uncompensated signal to the change. Examples of high glucose rates-of-change may include, but are not limited to, plus or minus 1 mg/dL per hour or greater, including plus or minus 2 mg/dL per hour, plus or minute 3 mg/dL per hour, etc. For example, criteria may include analyte level thresholds or ranges that are predetermined and programmed into an analyte monitoring system and used to determine when a transition should occur from tracking uncompensated to lag-compensated analyte levels, or vice versa. The various analyte thresholds may be different for transitions from uncompensated to lag-compensated analyte levels and for transitions from lag-compensated to uncompensated analyte levels.

The methods, devices, and systems may relate to one or more components of an analyte monitoring system, such as continuous analyte monitoring systems, including an in vivo analyte sensor, a sensor electronics unit that receives analyte sensor data from the in vivo analyte sensor, and a receiver unit that receives analyte sensor data from the sensor electronics unit. A display may also be included with the sensor electronics unit or receiver unit. Other components and devices may also be implemented in the system, such as medication delivery devices (e.g., insulin delivery devices), etc.

In some aspects of the present disclosure, methods of generating a hybrid analyte level output are provided. The methods include receiving sensor data which may be in vivo sensor data from an in vivo sensor, and generating a hybrid analyte level output including uncompensated analyte levels and lag-compensated analyte levels. The uncompensated analyte levels lag in time with respect to the lag-compensated analyte levels, and the hybrid analyte level output tracks between the uncompensated analyte levels and the lag-compensated analyte levels according to predetermined criteria. The term "track", 'tracks", "tracking", or the like, is used broadly herein, and may include using the actual signal levels (e.g., by switching between the two, etc.), duplicating or reproducing the signals, calculating the signals, approximating the signals, imitating or simulating the signals, following or otherwise resembling the signals, etc. This may also include instances where one or both of the lag-compensated and uncompensated signal levels are calculated for the purpose of generating the hybrid output only, and not necessarily generated as a separate stand-alone signal itself. In certain embodiments where both the lag-compensated and uncompensated signals are generated, the hybrid output may include, for example, using the lag-compensated and uncompensated signals or levels by switching between the actual lag-compensated and uncompensated signals to form the hybrid output—e.g., displaying the generated uncompensated signal when tracking the uncompensated signal, and displaying the lag-compensated signal when tracking the lag-compensated signal. In certain embodiments, the hybrid output signal may include generating a signal that reproduces, approximates, simulates, calculates, etc., the lag-compensated and uncompensated signals, and then the generated hybrid analyte output signal is outputted on display. In some instances, for example, the hybrid analyte level output may be generated from an uncompensated signal, to which lag-compensation may be activated and deactivated.

In some aspects of the present disclosure, analyte monitoring devices are provided. The analyte monitoring devices include a processor and memory operably coupled to the processor. The memory includes instructions stored therein to generate a hybrid analyte level output. The instructions include instructions for receiving sensor data which may be generated from an in vivo sensor, and instructions for generating a hybrid analyte level output including uncompensated analyte levels and lag-compensated analyte levels. The uncompensated analyte levels lag in time with respect to the lag-compensated analyte levels, and the hybrid analyte level output tracks between the uncompensated analyte levels and the lag-compensated analyte levels according to predetermined criteria.

In some aspects of the present disclosure, analyte monitoring systems are provided. The analyte monitoring systems include an analyte sensor which may be an in vivo sensor, an analyte monitoring device in communication with the analyte sensor, a processor, and memory operably coupled to the processor. The memory includes instructions stored therein to generate a hybrid analyte level output. The instructions include instructions for receiving sensor data which may be in vivo sensor data from an in vivo sensor, instructions for calculating uncompensated analyte levels based on the sensor data, and instructions for generating a hybrid analyte level output including the uncompensated analyte levels and lag-compensated analyte levels. The uncompensated analyte levels lag in time with respect to the lag-compensated analyte levels, and the hybrid analyte level output tracks between the uncompensated analyte levels and the lag-compensated analyte levels according to predetermined criteria.

INCORPORATION BY REFERENCE

The following patents, applications and/or publications are incorporated herein by reference for all purposes: U.S. Pat. No. 7,041,468; U.S. Pat. No. 5,356,786; U.S. Pat. No. 6,175,752; U.S. Pat. No. 6,560,471; U.S. Pat. No. 5,262,035; U.S. Pat. No. 6,881,551; U.S. Pat. No. 6,121,009; U.S. Pat. No. 7,167,818; U.S. Pat. No. 6,270,455; U.S. Pat. No. 6,161,095; U.S. Pat. No. 5,918,603; U.S. Pat. No. 6,144,837; U.S. Pat. No. 5,601,435; U.S. Pat. No. 5,822,715; U.S. Pat. No. 5,899,855; U.S. Pat. No. 6,071,391; U.S. Pat. No. 6,120,676; U.S. Pat. No. 6,143,164; U.S. Pat. No. 6,299,757; U.S. Pat. No. 6,338,790; U.S. Pat. No. 6,377,894; U.S. Pat. No. 6,600,997; U.S. Pat. No. 6,773,671; U.S. Pat. No. 6,514,460; U.S. Pat. No. 6,592,745; U.S. Pat. No. 5,628,890; U.S. Pat. No. 5,820,551; U.S. Pat. No. 6,736,957; U.S. Pat. No. 4,545,382; U.S. Pat. No. 4,711,245; U.S. Pat. No. 5,509,410; U.S. Pat. No. 6,540,891; U.S. Pat. No. 6,730,200; U.S. Pat. No. 6,764,581; U.S. Pat. No. 6,299,757; U.S. Pat. No. 6,461,496; U.S. Pat. No. 6,503,381; U.S. Pat. No. 6,591,125; U.S. Pat. No. 6,616,819; U.S. Pat. No. 6,618,934; U.S. Pat. No. 6,676,816; U.S. Pat. No. 6,749,740; U.S. Pat. No. 6,893,545; U.S. Pat. No. 6,942,518; U.S. Pat. No. 6,514,718; U.S. Pat. No. 5,264,014; U.S. Pat. No. 5,262,305; U.S. Pat. No. 5,320,715; U.S. Pat. No. 5,593,852; U.S. Pat. No. 6,746,582; U.S. Pat. No. 6,284,478; U.S. Pat. No. 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Application Publication No. US2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; US patent Application Publication No. 2010/0198034; US patent Application Publication No. 2008/0081977; US patent Application Publication No. 2009/0198118; and U.S. provisional application No. 61/149,639 titled "Compact On-Body Physiological Monitoring Device and Methods Thereof", the disclosures of each of which are incorporated herein by reference in their entirety.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

DETAILED DESCRIPTION

Figure 2:
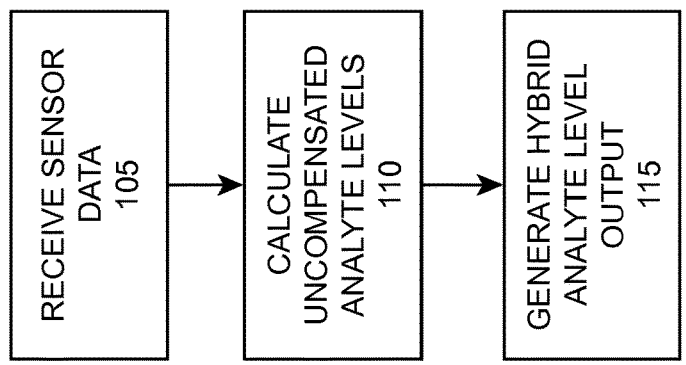
FIG. 2 illustrates a flowchart of a method for generating a hybrid analyte level output, according to one embodiment.

Before the embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the embodiments of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the present disclosure. The upper and lower limits of these smaller ranges may independently be included or excluded in the range, and each range where either, neither or both limits are included in the smaller ranges is also encompassed within the present disclosure, subject to any specifically excluded limit in the stated range. Where the stated range includes one or both of the limits, ranges excluding either or both of those included limits are also included in the present disclosure.

In the description of the present disclosure herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the present disclosure. It will be understood that a corresponding description of these various terms applies to corresponding linguistic or grammatical variations or forms of these various terms. It will also be understood that the present disclosure is not limited to the terminology used herein, or the descriptions thereof, for the description of particular embodiments. Merely by way of example, the present disclosure is not limited to particular analytes, bodily or tissue fluids, blood or capillary blood, or sensor constructs or usages, unless implicitly or explicitly understood or stated otherwise, as such may vary. The publications discussed herein are provided solely for their disclosure prior to the filing date of the application. Nothing herein is to be construed as an admission that the embodiments of the present disclosure are not entitled to antedate such publication by virtue of prior invention. Further, the dates of publication provided may be different from the actual publication dates which may need to be independently confirmed.

The term "processor" is used broadly herein, and may include any type of programmable or non-programmable processing device, such as a microprocessor, microcontroller, application-specific integrated circuits (ASICS), programmable logic devices (PLDs), field-programmable gate arrays (FPGAs), etc. The term "processor" may also include multiple processing devices working in conjunction with one another.

As summarized above, in some aspects of the present disclosure, methods, devices, and systems related to generating a hybrid analyte level output are provided. The hybrid analyte level output includes both uncompensated analyte levels and lag-compensated analyte levels that are based off sensor data derived from an in vivo positioned analyte sensor. Predetermined criteria may be used to determine when the hybrid analyte level output tracks uncompensated analyte levels or lag-compensated analyte levels.

Glucose levels taken from interstitial fluid (ISF) lag in time behind blood glucose levels. Lag-compensation techniques may be used to lag-compensate the ISF analyte levels to more closely approximate blood glucose levels. In this way, uncompensated analyte levels (e.g., ISF analyte level) may be lag-compensated (e.g., by applying a lag-compensation filter) to generate a lag-compensated analyte levels (e.g., an approximation of blood glucose levels).

In some circumstances, however, an ISF analyte level may be more appropriate or desirable. For example, ISF glucose may be more representative of how a person feels—e.g., during hypoglycemia or hyperglycemia or when approaching hypo- or hyper-glycemia. Thus, if a patient's blood glucose level rises after being hypoglycemic, the patient may falsely assume they are "safe" when in actuality their ISF glucose level is lagging and may still be low.

Blood glucose levels, however, may be more appropriate or desirable. For example, blood glucose levels may act as a precursor to where the ISF glucose will eventually be, and are therefore useful in other scenarios. For instances, as glucose levels are falling to a low value, a patient that gets a low blood glucose reading may know ahead of time that they will soon start feeling unwell, as their ISF glucose later gets low.

In some aspects of the present disclosure, hybrid analyte level outputs (also referred to herein as "hybrid output") are provided that include uncompensated analyte levels (e.g., ISF glucose levels) and lag-compensated analyte levels (e.g., approximations of blood glucose, also referred to hereafter as "blood glucose", achieved by lag-compensation techniques).

The hybrid outputs may include uncompensated analyte levels and lag-compensated analyte levels in various manners, as will be demonstrated and described herein. For example, in one embodiment, a hybrid analyte level output may be designed to track uncompensated analyte levels (e.g., ISF glucose levels) when the glucose is low and rising; otherwise, the hybrid output tracks blood glucose (e.g., approximations of blood glucose achieved by lag-compensation techniques). The transitions between uncompensated analyte levels and lag-compensated analyte levels may, for instance, be made smooth by implementing a smoothing function, such as a weighted combination of the uncompensated analyte levels and lag-compensated analyte levels. The embodiments provided in the following paragraphs are exemplary and the scope of the present disclosure should not be construed as limited to the exemplary embodiments. Further, the features described in one embodiment may be equally applicable in another embodiment.

Figure 1:
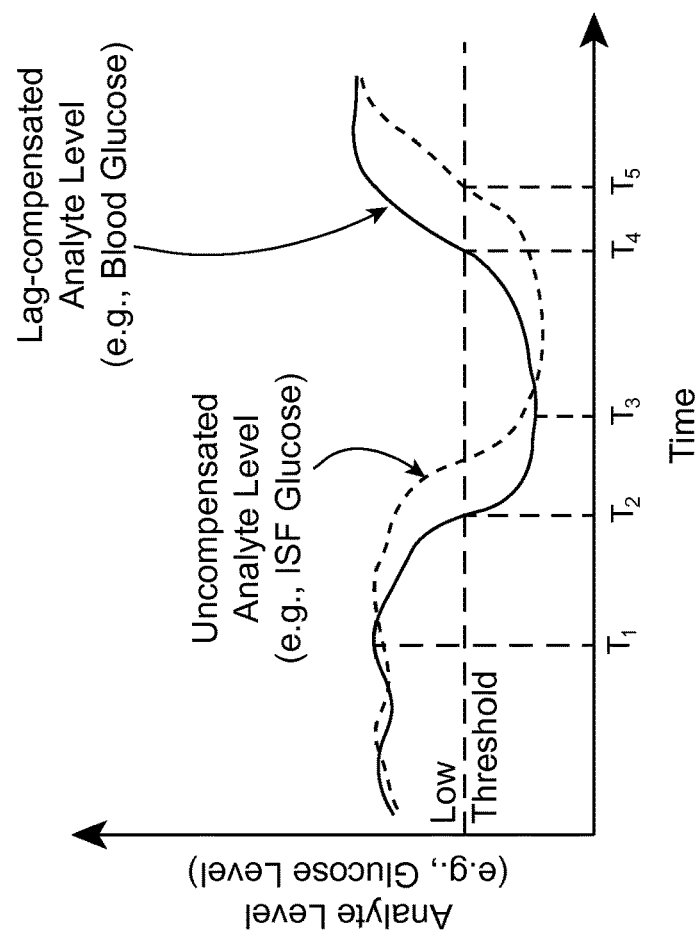
FIG. 1 illustrates a chart simultaneously displaying an uncompensated analyte level and a lag-compensated analyte level tracked over time for a patient.

FIG. 1 illustrates a chart simultaneously displaying an uncompensated analyte level (e.g., ISF glucose level) and a lag-compensated analyte level (e.g., approximation of blood glucose level) tracked over time for a patient. The chart illustrates that ISF glucose level lags the blood glucose level. The glucose value is represented on one axis and time represented on the other axis. The blood glucose and ISF glucose are shown as a solid line and dotted line, respectively. Before time T1, the patient's glucose level is approximately constant and thus the blood glucose and the ISF glucose are approximately the same value. When the patient's blood glucose level drops at time T1, the ISF glucose lags behind and drops after some time period of delay after the blood glucose.

Thus, for example, when the blood glucose drops to the low threshold line shown in the chart, as represented at time T2, the ISF glucose is still at a higher glucose value than the threshold value and will reach the threshold line after some delay in time. At time T3, the patient's blood glucose level flattens out and begins to rise again. As the ISF glucose is lagging the blood glucose, the ISF glucose is still trending downward and will flatten out and rise after a certain delay in time.

At time T4, the blood glucose reaches the threshold line with the ISF glucose still lagging and at a lower glucose value than the threshold value. The ISF glucose reaches the threshold line at time T5, after some delay in time from when the blood glucose reaches the threshold line.

FIG. 2 illustrates a flowchart of a method for generating a hybrid analyte level output, according to one embodiment. At block 105, sensor data is received. The sensor data may be originally derived from a transcutaneously positioned sensor that communicates the sensor data to an analyte monitoring device. The analyte monitoring device may include any data processing device that is used to monitor analytes. For example, the analyte monitoring device may include, but is not limited to, a glucose meter, personal computer, a portable computer including a laptop or a handheld device such as a consumer electronic device (e.g., a personal digital assistant (PDA), a telephone including a cellular phone (e.g., a multimedia and Internet-enabled mobile phone including an iPhone™, a Blackberry®, or similar phone), an mp3 player (e.g., an iPOD™ etc.), a pager, and the like), and/or a drug delivery device (e.g., a medication delivery pump). The analyte monitoring device may, for example, include software necessary to perform the analyte monitoring techniques described herein. The analyte monitoring device may receive sensor data originating from the in vivo positioned sensor either directly or via another data processing device.

In one embodiment, the in vivo positioned sensor is positioned in interstitial fluid such that a sensing portion resides below the skin and an electrical contact portion resides above (i.e., transcutaneously), and provides sensor data continuously to the analyte monitoring device (e.g., such as in continuous glucose monitoring (CGM) systems). In another embodiment, the in vivo sensor may provide sensor data upon interrogation by a hand-held unit (e.g., such as intermittently or periodically interrogated analyte sensing systems), for example using radio frequency identification technologies or the like.

At block 110, uncompensated analyte levels are calculated from the sensor data. For example, a processor on the analyte monitoring device may receive sensor data and calculate an uncompensated analyte level from the sensor data. In such case, the sensor data is raw sensor data acquired by the analyte sensor, for example as current, voltage, or the like.

In another embodiment, the sensor data that is received in block 105 includes the uncompensated analyte level, and thus block 110 is not included. For instance, an analyte sensor positioned in interstitial fluid may generate raw sensor data, and further include electronic circuitry to calculate the uncompensated analyte level and transmit it to an analyte monitoring device as sensor data. The analyte monitoring device receives the sensor data including the uncompensated analyte level and generates the hybrid analyte level output.

At block 115, a hybrid analyte level output is generated that includes uncompensated analyte levels and lag-compensated analyte levels. Uncompensated analyte levels calculated from sensor data derived from interstitial fluid will lag in time with respect to the actual analyte level of the blood. In order to more closely approximate the analyte level of the blood, the uncompensated analyte level may be lag compensated (e.g., by applying a lag-compensation filter to the uncompensated analyte level), resulting in a lag-compensated analyte level. Thus, the uncompensated analyte levels lag in time with respect to the lag-compensated analyte levels.

The hybrid analyte level output tracks between the uncompensated analyte levels and the lag-compensated analyte levels according to predetermined criteria. The predetermined criteria may include criteria that specifically define when the hybrid analyte level output tracks the uncompensated analyte levels and the lag-compensated analyte levels. This determination may be made, for example, by the processor of the analyte monitoring device mentioned above. When the processor determines that the predetermined criteria for tracking uncompensated analyte levels are met, the hybrid analyte level output will track uncompensated analyte levels. When the processor determines that the predetermined criteria for tracking lag-compensated analyte levels are met, the hybrid analyte level output will track lag-compensated analyte levels.

Figure 3:
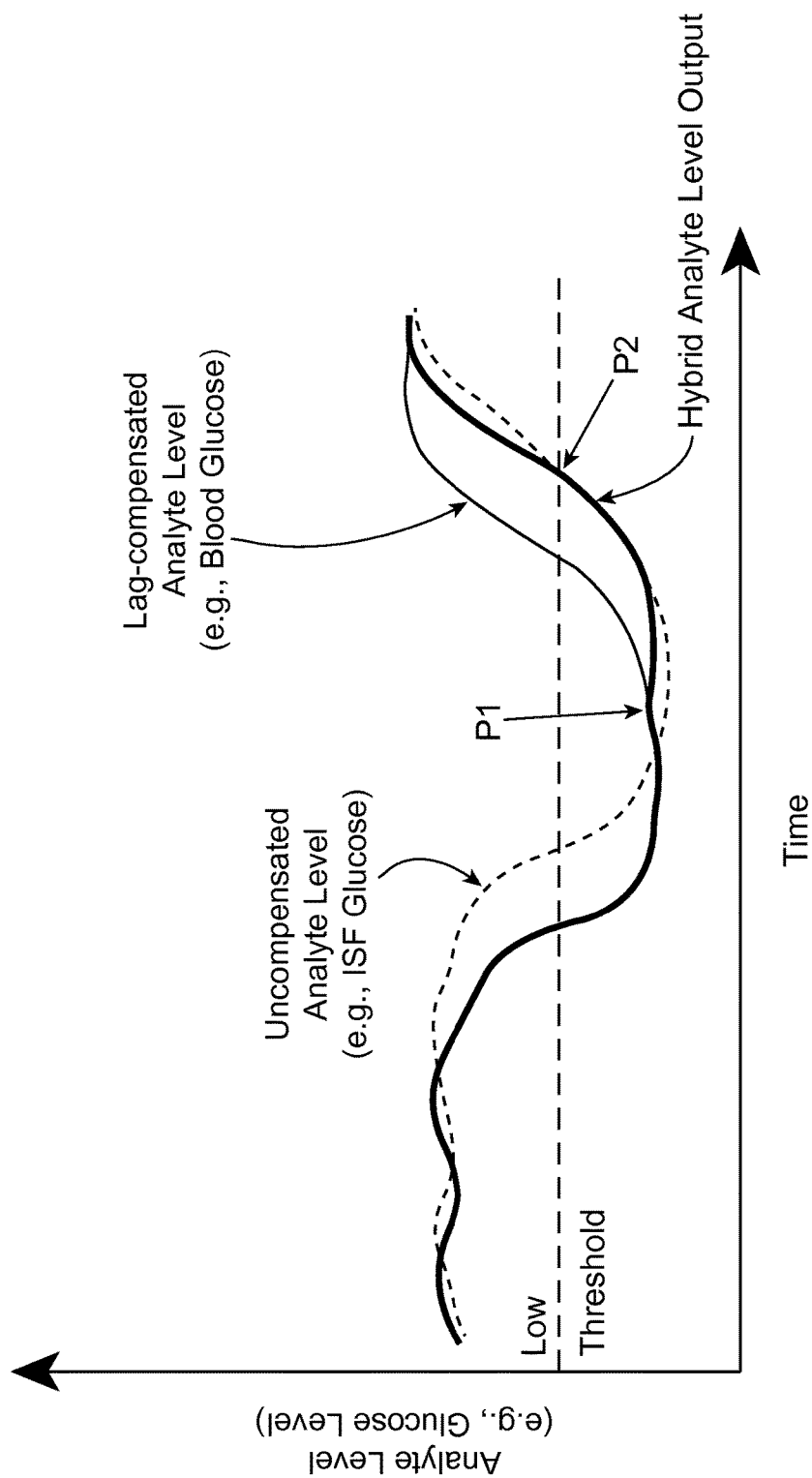
FIG. 3 illustrates a chart of a hybrid analyte level output, according to one embodiment.

FIG. 3 illustrates a chart of a hybrid analyte level output, according to one embodiment. The hybrid analyte level output tracks between the uncompensated analyte level (e.g., ISF glucose level) and the lag-compensated analyte level (e.g., approximation of blood glucose level) according to predetermined criteria, which will be described in further detail later. As shown, the exemplary hybrid analyte level output begins tracking the lag-compensated analyte level and continues to track the lag-compensated analyte level until predetermined criteria are met for switching to the uncompensated analyte level, as represented at point P1. Thereafter, the hybrid output will track the uncompensated analyte levels until predetermined criteria are met for tracking the lag-compensated analyte levels, as represented at point P2.

In the example shown, smoothing functions are implemented at each transition between lag-compensated analyte levels and uncompensated analyte levels. The smoothing function may, for example, include weighted combinations of the lag-compensated analyte levels and uncompensated analyte levels at these transition points, such that the hybrid analyte level output includes both the lag-compensated analyte levels and uncompensated analyte levels which are weighted in a particular manner. For instance, the weighting of the lag-compensated analyte levels and uncompensated analyte levels varies over time during the transition. For example, transitioning form lag-compensated analyte levels to uncompensated analyte levels may begin with a one hundred percent weighting on the lag-compensated analyte levels and zero percent weighting on the uncompensated analyte levels; then, over the duration of the transition period, decreasing the weighting on the lag-compensated analyte levels while increasing the weighting on the uncompensated analyte levels; and finally ending the transition with zero percent weighting on the lag-compensated analyte levels and one hundred percent weighting on the uncompensated analyte levels. A similar weighting scheme may apply to transition from uncompensated analyte levels to lag-compensated analyte levels, such that the weighting on the uncompensated analyte levels begins at one hundred percent and decreases to zero percent while the weighting on the lag-compensated analyte levels begins at zero percent and increases to one hundred percent. Instantaneous jumps and large breaks between the lag-compensated analyte levels and uncompensated analyte levels are thus avoided. For example, at point P1, predetermined criteria are met for switching to the uncompensated analyte level. At this point, a smoothing function (e.g., which incorporates weighted combinations of the uncompensated and lag-compensated analyte levels) is implemented for the transition from lag-compensated analyte levels to uncompensated analyte levels, and the hybrid output smoothly switches from the lag-compensated analyte levels to the uncompensated analyte levels. In different embodiments, smoothing functions, such as ones using weighted combinations, may be implemented at one or both transition points, and further, may implement the same or different smoothing functions at the two transitions points.

Figure 4:
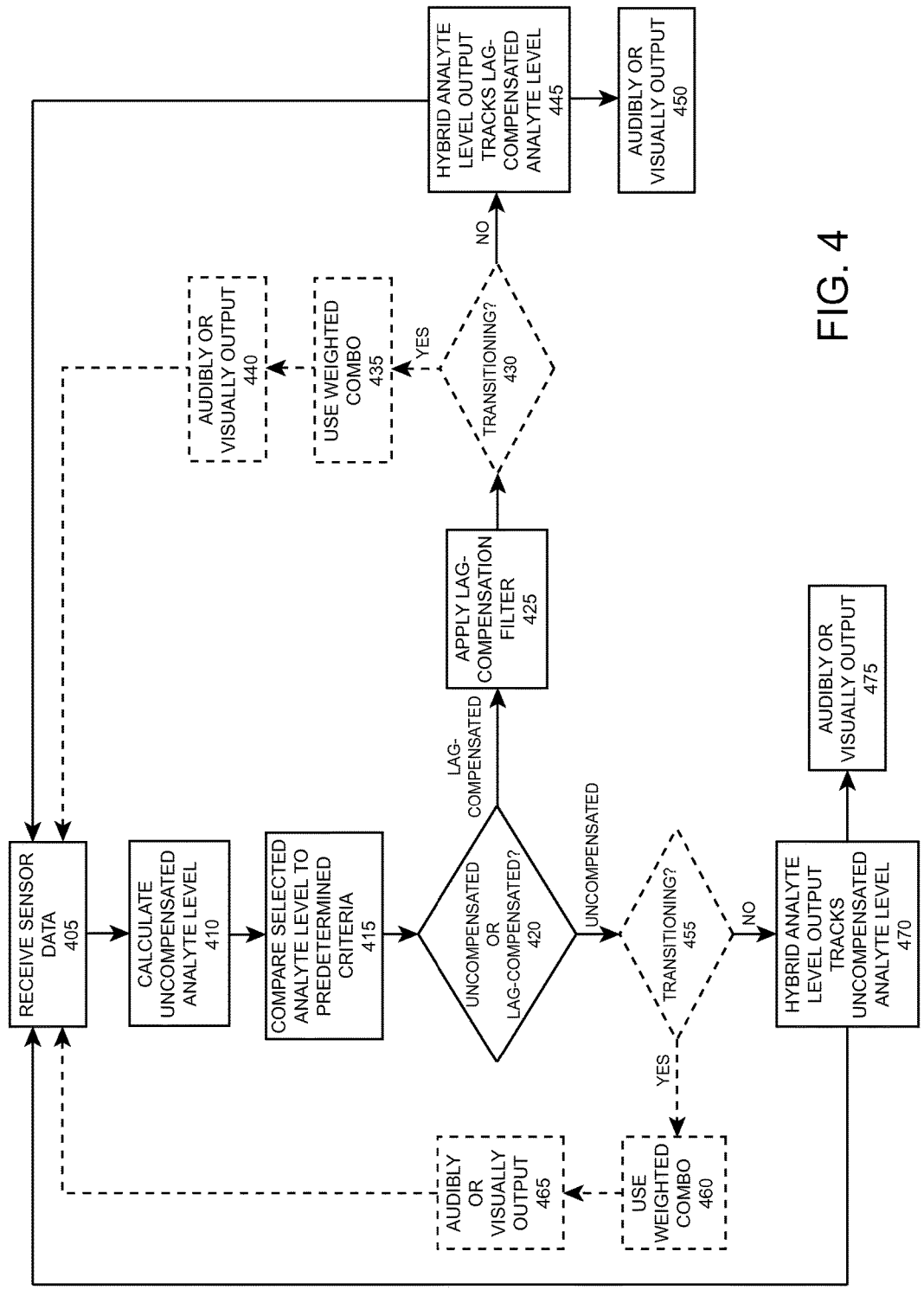
FIG. 4 illustrates a flowchart for a method of generating a hybrid analyte level output, according to one embodiment.

FIG. 4 illustrates a flowchart for a method of generating a hybrid analyte level output, according to one embodiment. In some instances, such as with CGM systems and intermittent or periodic interrogation analyte sensing systems, sensor data continues to be received over time. The method shown in FIG. 4 illustrates one cycle that may be repeated as new sensor data is continuously acquired over time from an in vivo positioned sensor and transmitted to a receiver, for example. To facilitate explanation, the method FIG. 4 is described with reference to a cycle of operations at time, t(1). The next cycle would be at time, t(2); and the next cycle at time, t(3); and so on for t(n) cycles. Moreover, the previous cycle would be at time, t(0).

At block 405, sensor data is received. For example, the sensor data may be originally derived from a transcutaneously positioned sensor that communicates the sensor data to an analyte monitoring device, such as described above. For example, at least a portion of an in vivo sensor may be positioned in interstitial fluid and provide sensor data continuously and automatically to the analyte monitoring device (e.g., such as in CGM systems). In another embodiment, the in vivo positioned sensor may provide sensor upon interrogation by a hand held device (e.g., such intermittent or periodic interrogation analyte sensing systems). The sensor data may be "raw", meaning that it would need to be processed to represent the analyte level. For instance, the raw sensor data may need to be multiplied by a conversion factor to represent an analyte level. Furthermore, an analyte level may be determined, sometimes in the form of a filter, from the most recently received sensor data in conjunction with one or more historical sensor data retrieved from memory.

At block 410, an uncompensated analyte level is calculated from the sensor data. For example, a processor on the analyte monitoring device may receive sensor data periodically and calculate the uncompensated analyte level from the sensor data. In one embodiment, the analyte monitoring device may include an electronic sensor control unit having the processor and electrically coupled to an in vivo positioned sensor, for example. The processor receives the sensor data derived from the in vivo positioned sensor, for instance. In another embodiment, the analyte monitoring device may include a receiver having a processor and communicably coupled to an electronic sensor control unit that is coupled to an in vivo positioned sensor. For instance, the sensor control unit transmits sensor data derived from the in vivo positioned sensor to the receiver, and ultimately the processor within the receiver.

In another embodiment, the sensor data that is received in block 405 includes the uncompensated analyte level, and thus block 410 is not included. For instance, an analyte sensor positioned in interstitial fluid may generate raw sensor data, and further include electronic circuitry to calculate the uncompensated analyte level and transmit it to an analyte monitoring device as sensor data. The analyte monitoring device receives the sensor data including the uncompensated analyte level and generates the hybrid analyte level output.

At block 415, a selected analyte level is compared to predetermined criteria to determine whether the hybrid output should track uncompensated analyte levels or lag-compensated analyte levels. Any variety of sources may be used as the selected analyte level. For instance, example sources may include, but are not limited to, lag-compensated analyte levels, uncompensated analyte levels, hybrid outputs, etc. Furthermore, the selected analyte level may apply to a specific occurrence of those analyte levels, such as the most recently generated analyte level. For example, in certain instances, the selected analyte level may be the most recently generated uncompensated analyte level, or the most recently generated lag-compensated analyte level. In other instances, the selected analyte level may be the most recently generated hybrid output.

The term "most recently" and "most recent" and the like refer to the last occurrence. For example, when at block 415, the most recently calculated uncompensated analyte level would refer to the level calculated at block 410 in the current cycle at time, t(1); the most recently generated lag-compensated analyte level would refer to the level calculated at block 425 in the previous cycle at time, t(0), the most recently generated hybrid output would refer to the level calculated at either blocks 445 or 470 in the previous cycle at time, t(0). In another embodiment, the transitional output levels (e.g., weighted combinations of uncompensated analyte levels and lag-compensated analyte levels) of the hybrid output may also be used as the selected analyte level, and thus the most recently generated hybrid output may also refer to the analyte levels calculated at either blocks 435 or 460 in the previous cycle at time, t(0).

One or more sources may be used as a selected analyte level in different circumstances in an embodiment. In one embodiment, only one source may be used at all times. For example, in one embodiment, the selected analyte level may always be the most recently calculated uncompensated analyte level. In another embodiment, the selected analyte level may always be the most recent lag-compensated analyte level. In yet another embodiment, the selected analyte level may always be the most recently generated analyte level for the hybrid output. The term "selected" is used broadly herein and may include a selection from multiple sources if multiple sources are implemented, or a selection of a single source that is used at all times.

In one embodiment, the selected analyte level that is used may vary from cycle to cycle. For example, the selected analyte level may depend on factors from the current cycle, previous cycle, etc. For instance, the selected analyte level may be selected based on whether the most recently generated hybrid output was an uncompensated or lag-compensated analyte level; or whether the hybrid output is transitioning. The selected analyte level may be selected based on a variety of factors, such as, but not limited to, the analyte rate-of-change, direction of analyte rate-of-change, acceleration of the rate, analyte level (e.g., above or below a threshold value), durations of time, etc. A variety of permutations and combinations of one or more of the various circumstances and factors may be implemented in various embodiments. Some exemplary selection schemes are described in further detail later.

The predetermined criteria may include criteria for tracking uncompensated analyte levels, for example. When this criteria is met, the hybrid output will track the uncompensated analyte levels. The predetermined criteria may also include criteria for tracking lag-compensated analyte levels. When this criteria is met, the hybrid output will track the lag-compensated analyte levels. For example, the lag-compensated analyte level may be generated by applying a lag-compensation filter to the uncompensated analyte level.

In one embodiment, the criteria for tracking uncompensated analyte levels are the negative of the criteria for tracking lag-compensated analyte levels. In other words, if the criteria for tracking uncompensated analyte levels are not met, then the criteria for tracking the lag-compensated analyte levels are met. For example, in one embodiment, the predetermined criteria include criteria for tracking the uncompensated analyte levels when selected analyte levels are below a predetermined threshold and have been rising for a predetermined duration of time. When this criteria is not met (i.e., selected analyte levels are not below a predetermined threshold or have not been rising for a predetermined duration of time), then the hybrid output tracks the lag-compensated analyte levels.

In another embodiment, the criteria for tracking lag-compensated analyte levels may not necessarily be the negative of the uncompensated analyte levels, as will be described in further detail later. For example, separate and different criteria may be defined for switching in each direction.

At block 420, it is determined whether criteria are met for tracking uncompensated analyte levels or lag-compensated analyte levels. If criteria for tracking lag-compensated analyte levels are met, then the uncompensated analyte level is lag compensated (e.g., by applying a lag compensation filter to the uncompensated analyte level) to generate the lag-compensated analyte level, as represented by block 425. The lag-compensated analyte level is then used for the hybrid output, as represented by block 445. The hybrid output may be output audibly or visually for the user—e.g., via a speaker or display on the analyte monitoring device—as represented by block 450. This may include outputting the hybrid output both audibly and visually in some instances.

In one embodiment, a smoothing function may be implemented between transitions from uncompensated analyte levels to lag-compensated analyte levels, as represented by blocks 430, 435, and 440. At block 430, a determination is made as to whether the hybrid output is transitioning from uncompensated analyte levels. If it is determined that the hybrid output is not transitioning, then the hybrid analyte level output tracks the lag-compensated analyte level as shown in block 445. For example, if the hybrid output was previously tracking the lag-compensated analyte level, then it will be determined that the hybrid output is not transitioning from uncompensated analyte levels to lag-compensated analyte levels. The transitioning period may vary in length or time in different embodiments.

However, if it is determined at block 430 that the hybrid output is transitioning from uncompensated analyte levels (e.g., the hybrid output has been tracking uncompensated analyte levels, or is at a transitional value during the transition process from uncompensated analyte levels to lag-compensated analyte levels), then a smoothing function will be implemented (or continued to be implemented). For example, at block 435, a weighted combination of the uncompensated analyte level and a lag-compensated analyte level is used to generate the hybrid output. The weighted combination may vary over the transition period—e.g., such that the weighting of the lag-compensated analyte levels and the uncompensated analyte levels vary throughout the duration of the transition period. The hybrid output may then be output audibly or visually via a speaker or display, as represented by block 440.

Referring back to block 420, if it is determined that the criteria for tracking uncompensated analyte levels are met, then the uncompensated analyte level is used for the hybrid output, thus making the hybrid output track the uncompensated analyte level, as represented by block 470. The hybrid output may then be output audibly or visually for the user—e.g., via a speaker or display on the analyte monitoring device—as represented by the block 475. Again, this may include outputting the hybrid output both audibly and visually in some instances.

In one embodiment, a smoothing function may be implemented between transitions to uncompensated analyte levels from lag-compensated analyte levels, as represented by blocks 455, 460, and 465. At block 455, it is determined whether the hybrid output is transitioning from uncompensated analyte levels. If it is determined that the hybrid output is not transitioning, then the hybrid analyte level output tracks the uncompensated analyte level, as shown in block 470. For example, if the hybrid output was previously tracking the uncompensated analyte level, then it will be determined that the hybrid output is not transitioning from lag-compensated analyte levels to uncompensated analyte levels. The transitioning period may vary in length or time in different embodiments.

However, if it is determined at block 455 that the hybrid output is transitioning from lag-compensated analyte levels (e.g., the hybrid output has been tracking lag-compensated analyte levels, or is at a transitional value during the transition process from lag-compensated analyte levels to uncompensated analyte levels), then a smoothing function will be implemented (or continued to be implemented). For example, at block 460, a weighted combination of the uncompensated analyte level and a lag-compensated analyte level is used to generate the hybrid output. A lag-compensated filter is applied to the uncompensated analyte level at block 460 to generate the lag-compensated analyte level for the weighted combination. The hybrid output may then be output audibly or visually via a speaker or display, as represented by block 465. The cycle may then be repeated for time, t(2), as represented by the arrows returning to box 405 from boxes 440, 445, 465, and 475.

In another embodiment the lag-compensation may be performed at a different time than shown in FIG. 4. For example, in one embodiment, the lag-compensation filter is applied to the uncompensated analyte level after block 410 and before the comparison to the predetermined criteria at block 415. In this embodiment, a lag-compensated analyte level is generated for each cycle whether or not the hybrid output is determined to track uncompensated analyte levels or lag-compensated analyte levels. In such case, the lag-compensated analyte level generated may be used when the hybrid output tracks the lag-compensated analyte level (e.g., block 445) and when the weighted combinations are generated (e.g., blocks 435 and 460).

In some aspects, another signal may be presented on the user interface instead of the hybrid output signal, or in addition to the hybrid output signal. For example, in certain embodiments, the lag-compensated analyte level is provided on the user interface instead of the hybrid output. The hybrid output may be used, however, to drive a "low analyte level" (e.g., low glucose level) indicator on the user interface according to predetermined criteria. For example, a predetermined low analyte threshold (e.g., low glucose threshold) may be implemented, such that when the hybrid signal drops below the low analyte threshold, the indicator is asserted and presented to the user. For instance, in FIG. 3, the lag-compensated signal would be displayed on the display, and once the hybrid analyte level output dropped below the "low threshold", the "low analyte level" indicator is initiated and displayed on the display of the device. The low analyte threshold is also referred to herein as the "low-entering analyte threshold" to distinguish it from the "low-exiting analyte threshold", which may or may not be the same threshold value.

The indicator continues to be asserted until predetermined criteria are met—e.g., until the hybrid signal crosses above the "low threshold" described above. Other predetermined criteria may be defined. For example, the indicator may be unasserted when the hybrid signal crosses another predetermined "low-exiting analyte threshold" rather than the same "low threshold described above; when another signal (e.g., lag-compensated analyte level, uncompensated analyte signal, transition signal, etc.) crosses a predetermined low-exiting analyte threshold; etc. For instance, in another embodiment, the indicator continues to be asserted until the uncompensated level crosses above the threshold (see, e.g., T5 in FIG. 1). In this case, the generation of the hybrid signal is optional, and the weighted sum transition method is optional.

For example, in one embodiment, when the lag-compensated analyte levels (e.g., blood glucose levels) are displayed to the user, and when the lag-compensated analyte levels drop below a "low threshold" value, the indicator is asserted. When the uncompensated analyte levels (e.g., interstitial fluid glucose levels) crosses above the same threshold (or another predetermined low-exiting threshold), then the indicator is unasserted—e.g., until again asserted. In this way, the users see the lag-compensated glucose level, for example, but the low glucose indicator stays active for some time after the lag-compensated glucose crosses above the low glucose threshold (or other low-exiting glucose threshold if implemented).

In other embodiments, other signals (e.g., uncompensated analyte signals, transitions signals, hybrid output signal, etc.) may also be presented to the user instead of, or in addition to, the lag-compensated analyte signal as described above. Moreover, other signals (e.g., uncompensated analyte signal, lag-compensated analyte signal, etc.) may be used to drive a "low analyte level" (e.g., low glucose level) indicator on the user interface. Various combinations may be implemented in other embodiments based on the specific application, therapeutic purpose, etc.

Again the user interface may be, for example, a display and/or speaker on the analyte monitoring device. Any variety of indicators may be used—e.g., symbols, icons, text, graphical elements, gifs, video clips, etc.—and should represent to the user that the analyte level is low. For instance, examples of the indicator may include, but are not limited to, visual texts such as, "Warning—low glucose", "low glucose", "low", etc. An indicator may be visual, audible, and/or vibratory, for example.

Figure 5:
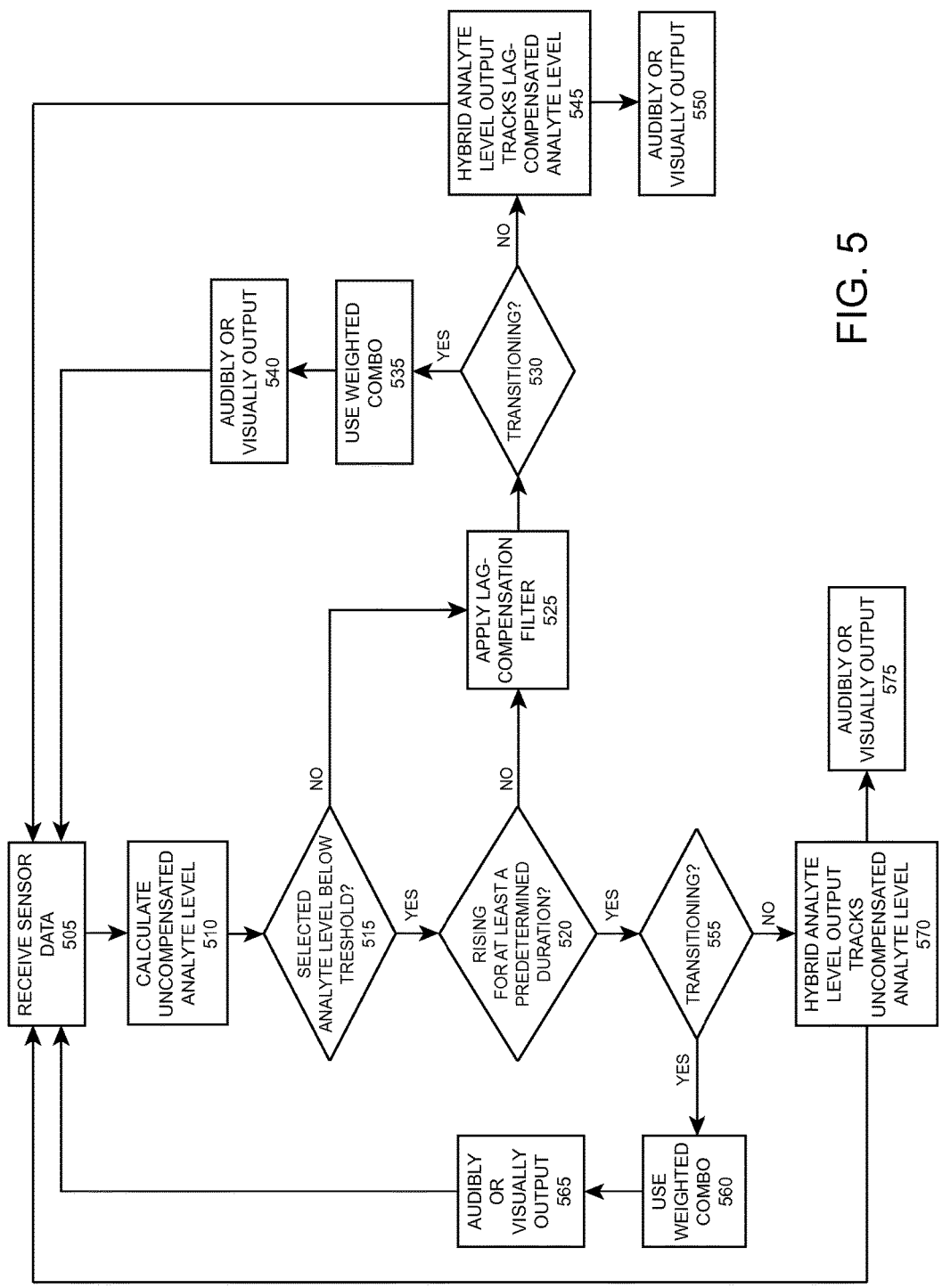
FIG. 5 illustrates a flowchart for a method of generating a hybrid analyte level output, according to one embodiment.

FIG. 5 illustrates a flowchart for a method of generating a hybrid analyte level output, according to one embodiment. Again, in some instances, such as with CGM systems and intermittent or periodic interrogation analyte sensing systems, sensor data continues to be received over time. The method shown in FIG. 5 illustrates one cycle that may be repeated as new sensor data is acquired. To facilitate explanation, FIG. 5 is described with reference to a cycle of operations at time, t(1). The next cycle would be at time, t(2); and the next cycle at time, t(3); and so on for t(n) cycles. Moreover, the previous cycle would be at time, t(0).

At block 505, sensor data is received. For example, the sensor data may be originally derived from a transcutaneously positioned sensor that communicates the sensor data to an analyte monitoring device. The positioned sensor is positioned in interstitial fluid and provides sensor data continuously to the analyte monitoring device (e.g., such as in CGM systems). In another embodiment, the positioned sensor may provide sensor upon interrogation by a held device (e.g., such as in intermittent or periodic interrogation analyte sensing systems).

At block 510, an uncompensated analyte level is calculated from the sensor data. For example, a processor on the analyte monitoring device may receive sensor data and calculate the uncompensated analyte level from the sensor data.

In another embodiment, the sensor data that is received in block 505 includes the uncompensated analyte level, and thus block 510 is not included. For instance, an analyte sensor positioned in interstitial fluid may generate raw sensor data, and further include electronic circuitry to calculate the uncompensated analyte level and transmit it to an analyte monitoring device as sensor data. The analyte monitoring device receives the sensor data including the uncompensated analyte level and generates the hybrid analyte level output.

In the embodiment shown in FIG. 5, the predetermined criteria includes criteria for tracking uncompensated analyte levels when selected analyte levels are below a predetermined threshold and have been rising for a predetermined duration of time, as represented by blocks 515 and 520. For this exemplary embodiment, the most recently generated lag-compensated analyte level is used as the selected analyte level to determine if the predetermined criteria are met.

When both of these two criteria are met (i.e., the selected analyte level is below a predetermined threshold and has been rising for a predetermined duration of time), the hybrid output tracks the uncompensated analyte levels. When either of these criteria are not met (i.e., selected analyte level is not below a predetermined threshold or has not been rising for a predetermined duration of time), the hybrid output tracks the lag-compensated analyte levels.

For example, at block 515, the selected analyte level is compared to a threshold value. The threshold value may, for instance, be a value that indicates hypoglycemia or other low glucose value. The most recently generated lag-compensated analyte level would be the lag-compensated analyte level that was generated in the previous cycle at time, t(0), at block 525.

If the selected analyte level (i.e., most recently generated lag-compensated analyte level) is not below the threshold value, then the criteria for tracking uncompensated analyte levels is not met and the hybrid output determined to track the lag-compensated analyte levels. A lag-compensation filter is then applied to the uncompensated analyte level to generate a lag-compensated analyte level, as represented by block 525.

If at block 515, the selected analyte level is below the threshold value, then it is determined whether the selected analyte level (i.e., most recently generated lag-compensated analyte level) has been rising for a predetermined duration of time, as represented at block 520. If the most recently generated lag-compensated analyte level has not been rising for a predetermined duration, then the criteria for tracking uncompensated analyte levels is not met and the hybrid output determined to track the lag-compensated analyte levels. A lag-compensation filter is then applied to the uncompensated analyte level to generate a lag-compensated analyte level, as represented by block 525.

After a lag-compensated analyte level is generated at block 525, it is determined whether the hybrid output is transitioning from uncompensated analyte levels to lag-compensated analyte levels, as represented by block 530. If it is determined that the hybrid output is not transitioning, then the hybrid analyte level output tracks the lag-compensated analyte level, as represented by block 545. For example, if the hybrid output was tracking a lag-compensated analyte level at time, t(0), then it will be determined that the hybrid output is not transitioning from uncompensated analyte levels to lag-compensated analyte levels. The hybrid output is then output audibly or visually for the user—e.g., via a speaker or display on the analyte monitoring device, as represented by block 550. This may include outputting the hybrid output both audibly and visually in some instances. The process is then repeated again for new sensor data at time, t(2), as represented by the arrow drawn from block 545 to block 505.

However, if it is determined at block 530 that the hybrid output is transitioning from uncompensated analyte levels to lag-compensated analyte levels (e.g., the hybrid output was tracking an uncompensated analyte level, or is at a transitional value during the transition process from uncompensated analyte levels to lag-compensated analyte levels), then a smoothing function is implemented (or continued to be implemented), as represented by block 535.

At block 535, a weighted combination of the uncompensated analyte level (calculated at block 510) and the lag-compensated analyte level (generated at block 525) is used as the hybrid output. The weighted combination may vary over the transition period—e.g., such that the weighting of the lag-compensated analyte level and the uncompensated analyte level vary throughout the duration of the transition period. The hybrid output may then be output audibly or visually via a speaker or display, as represented by block 540. The process is then repeated again for new sensor data at time, t(2), as represented by the arrow drawn from block 540 to block 505.

Referring back to block 520, if the selected analyte level (i.e., most recently generated lag-compensated analyte level) has been rising for a predetermined duration of time, then the criteria for tracking uncompensated analyte levels is met and the hybrid output is determined to track the uncompensated analyte levels. At block 555, it is determined whether the hybrid output is transitioning from lag-compensated analyte levels to uncompensated analyte levels. If it is determined that the hybrid output is not transitioning, then the hybrid analyte level output tracks the uncompensated analyte level, as represented by block 570. For example, if the hybrid output was tracking an uncompensated analyte level at time, t(0), then it will be determined that the hybrid output is not transitioning from lag-compensated analyte levels to uncompensated analyte levels. The hybrid output is then output audibly or visually for the user—e.g., via a speaker or display on the analyte monitoring device, as represented by block 575. This may include outputting the hybrid output both audibly and visually in some instances. The process is then repeated again for new sensor data at time, t(2), as represented by the arrow drawn from block 570 to block 505.

However, if it is determined at block 555 that the hybrid output is transitioning from lag-compensated analyte levels to uncompensated analyte levels (e.g., the hybrid output at time, t(0), was tracking a lag-compensated analyte level, or was at a transitional value during the transition process from lag-compensated analyte levels to uncompensated analyte levels), then a smoothing function is implemented (or continued to be implemented), as represented by block 560.

At block 560, a weighted combination of the uncompensated analyte level (calculated at block 510) and the lag-compensated analyte level is used as the hybrid output. A lag-compensated filter is applied to the uncompensated analyte level at block 560 to generate the lag-compensated analyte level. In another embodiment, the lag-compensated analyte level generated at block 525 of time, t(0), is used. The weighted combination may vary over the transition period—e.g., such that the weighting of the lag-compensated analyte level and the uncompensated analyte level vary throughout the duration of the transition period. The hybrid output may then be output audibly or visually via a speaker or display, as represented by block 565. The process is then repeated again for new sensor data at time, t(2), as represented by the arrow drawn from block 565 to block 505.

In another embodiment, the lag-compensation filter is applied to the uncompensated analyte level after block 510 and before the comparison to the predetermined criteria. A lag-compensated analyte level is thus generated for each cycle whether or not the hybrid output is determined to track uncompensated analyte levels or lag-compensated analyte levels. In such case, the lag-compensated analyte level generated may be used when the hybrid output tracks the lag-compensated analyte level (e.g., block 545) and when the weighted combinations are generated (e.g., blocks 535 and 560).

As similarly described above for FIG. 4, in some aspects, another signal may be presented on the user interface instead of the hybrid output signal, or in addition to the hybrid output signal. For example, in certain embodiments, the lag-compensated analyte levels are provided on the user interface instead of the hybrid output, and the hybrid output is used to drive a "low analyte level" (e.g., low glucose level) indicator on the user interface according to predetermined criteria. For the sake of brevity and clarity, the above discussion in FIG. 4 is not repeated here, but should be understood to be similarly applicable.

FIGS. 6-13 illustrate example transitions between lag-compensated analyte levels and uncompensated analyte levels. Only a portion of the graph associated with the described transition is shown in the figures, as denoted by the curved line breaks on each side of the analyte levels.

Figure 6A:
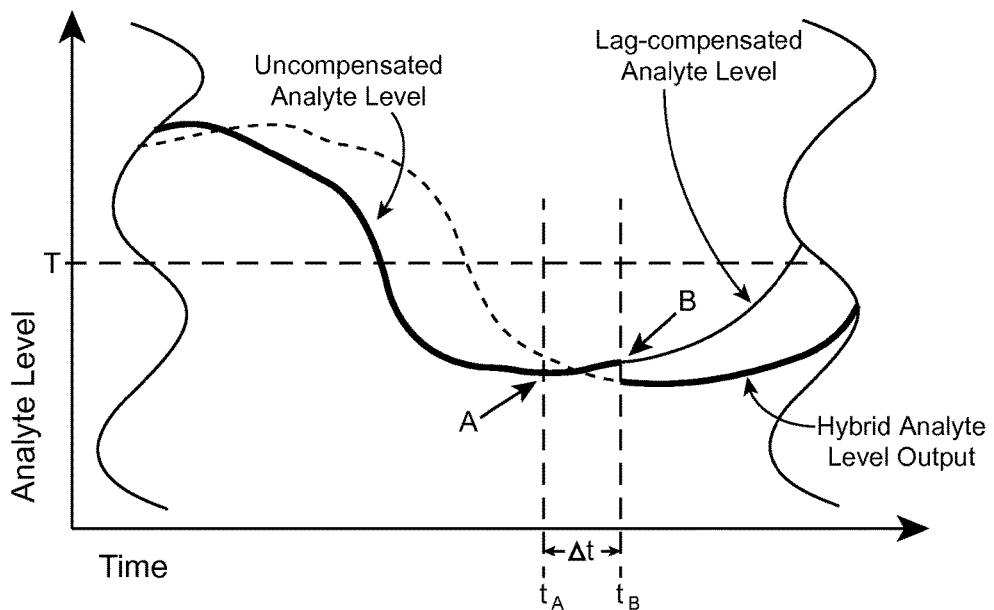
FIG. 6A illustrates a chart of a hybrid output as it transitions from lag-compensated analyte levels to uncompensated analyte levels, according to one embodiment.

FIG. 6A illustrates a chart of a hybrid output as it transitions from lag-compensated analyte levels to uncompensated analyte levels, according to one embodiment. For the exemplary embodiment shown, the predetermined criteria includes criteria for continuing to track the lag-compensated analyte levels until the selected analyte level is below the threshold value T and rising for a predetermined duration of time.

In the embodiment shown, the graph begins with the hybrid output tracking the lag-compensated analyte level, and the most recently calculated lag-compensated is used as the selected analyte level for comparison to the predetermined criteria. The lag-compensated analyte level (and thus selected analyte level) is above the predetermined threshold. Thus, the criteria for tracking the lag-compensated analyte level is still met.

Thus, as shown, where the lag-compensated analyte level crosses below the threshold line T, the selected analyte level drops below the threshold line T but has not been rising for a predetermined duration of time. Thus, the criteria for tracking the lag-compensated analyte level is still met.

At point A (time=$t_A$), the lag-compensated analyte level (and thus selected analyte level) is below the threshold value and begins to rise. However, the lag-compensated analyte levels have not been rising for a predetermined duration of time (e.g., $\Delta t$). Thus, the criteria for tracking the lag-compensated analyte level is still met.

At point B (time=$t_B$), the lag-compensated analyte level (and thus selected analyte level) has been rising for the predetermined duration of time (e.g., $\Delta t$) and is also below the threshold value T. Thus, the selected analyte level now meets the predetermined criteria for the hybrid output to track the uncompensated analyte level. As shown in the graph, the hybrid output tracks the uncompensated analyte levels at time $t_B$. In the embodiment shown, no smoothing function is implemented and thus the hybrid output jumps from the lag-compensated analyte levels to the uncompensated analyte levels.

After the hybrid output begins tracking the uncompensated analyte levels, a selected analyte level is compared to the predetermined criteria to determine when to stop tracking the uncompensated analyte levels and to start tracking the lag-compensated analyte levels again. The selected analyte level may or may not be derived from the same source after the transition. For example, in one embodiment, the most recently generated lag-compensated analyte level continues to be used as the selected analyte level that is compared to the predetermined criteria. In another embodiment, for example, the most recently calculated uncompensated analyte level may now be used as the selected analyte level that is compared to the predetermined criteria.

Figure 6B:
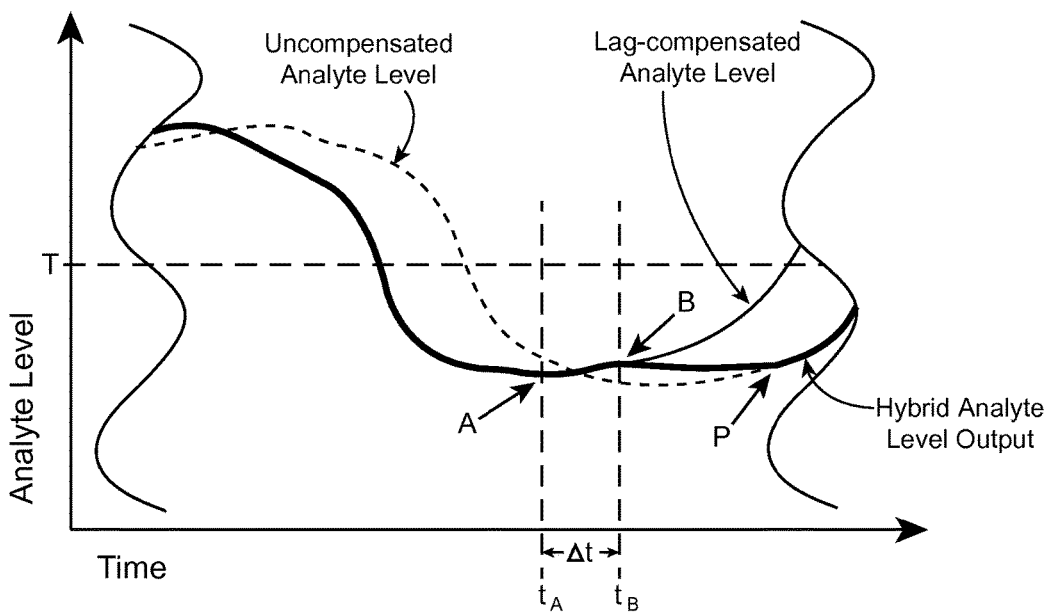
FIG. 6B illustrates a chart of a hybrid output as it transitions from lag-compensated analyte levels to uncompensated analyte levels, according to one embodiment.

FIG. 6B illustrates a chart of a hybrid output as it transitions from lag-compensated analyte levels to uncompensated analyte levels, according to one embodiment. The example embodiment shown in FIG. 6B differs from the example embodiment shown in FIG. 6A by having a smoothing function implemented for the transition. For the sake of brevity and clarity, only the transition period is discussed for FIG. 6B.

As similarly described above for FIG. 6A, at point B, the lag-compensated analyte level (and thus selected analyte level) is below the threshold value and has been rising for the predetermined duration of time (e.g., $\Delta t$). Thus, the criteria is now met for the hybrid output to stop tracking the lag-compensated analyte levels and to start tracking the uncompensated analyte levels. Since the hybrid output is transitioning, a smoothing function is applied to provide a smooth transition from the lag-compensated analyte levels to uncompensated analyte levels. For example, the smoothing function may include weighted combinations of lag-compensated and uncompensated analyte levels that vary over the transition period. At point P, the hybrid output has completely transitioned to the uncompensated analyte levels and the smoothing function is no longer applied.

Figure 7A:
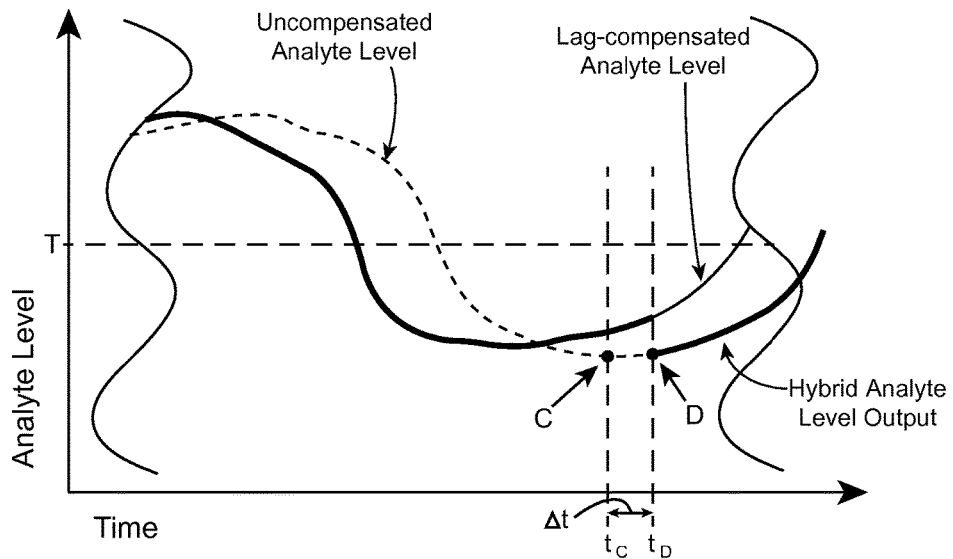
FIG. 7A illustrates a chart of a hybrid output as it transitions from lag-compensated analyte levels to uncompensated analyte levels, according to one embodiment.

FIG. 7A illustrates a chart of a hybrid output as it transitions from lag-compensated analyte levels to uncompensated analyte levels, according to one embodiment. For the exemplary embodiment shown, the predetermined criteria includes criteria for continuing to track the lag-compensated analyte levels until the selected analyte level is below the threshold value T and rising for a predetermined duration of time.

In the embodiment of FIG. 7A, the graph begins with the hybrid output tracking the lag-compensated analyte level, and the most recently calculated uncompensated analyte level is used as the selected analyte level for comparison to the predetermined criteria. The uncompensated analyte level (and thus selected analyte level) is above the predetermined threshold. Thus, the criteria for tracking the lag-compensated analyte level is still met.

Thus, as shown, where the uncompensated analyte level crosses below the threshold line T, the selected analyte level drops below the threshold line T but has not been rising for a predetermined duration of time. Thus, the criteria for tracking the lag-compensated analyte level is still met.

At point C (time=$t_C$), the uncompensated analyte level (and thus selected analyte level) is below the threshold value and begins to rise. However, the uncompensated analyte levels have not been rising for a predetermined duration of time (e.g., $\Delta t$). Thus, the criteria for tracking the lag-compensated analyte levels is still met.

At point D (time=$t_D$), the uncompensated analyte level (and thus selected analyte level) has been rising for the predetermined duration of time (e.g., $\Delta t$) and is also below the threshold value T. Thus, the selected analyte level now meets the predetermined criteria for the hybrid output to track the uncompensated analyte level. As shown in the graph, the hybrid output tracks the uncompensated analyte level at point D. In the embodiment shown, no smoothing function is implemented and thus the hybrid output jumps from the lag-compensated analyte levels to the uncompensated analyte levels.

After the hybrid output begins tracking the lag-compensated analyte levels, a selected analyte level is compared to the predetermined criteria to determine when to stop tracking the uncompensated analyte levels and to start tracking the lag-compensated analyte levels again. The selected analyte level may or may not be derived from the same source after the transition. For example, in one embodiment, the most recently calculated uncompensated analyte level continues to be used as the selected analyte level that is compared to the predetermined criteria. In another embodiment, for example, the most recently generated lag-compensated analyte level, or the most recently generated hybrid output, may now be used as the selected analyte level that is compared to the predetermined criteria.

Figure 7B:
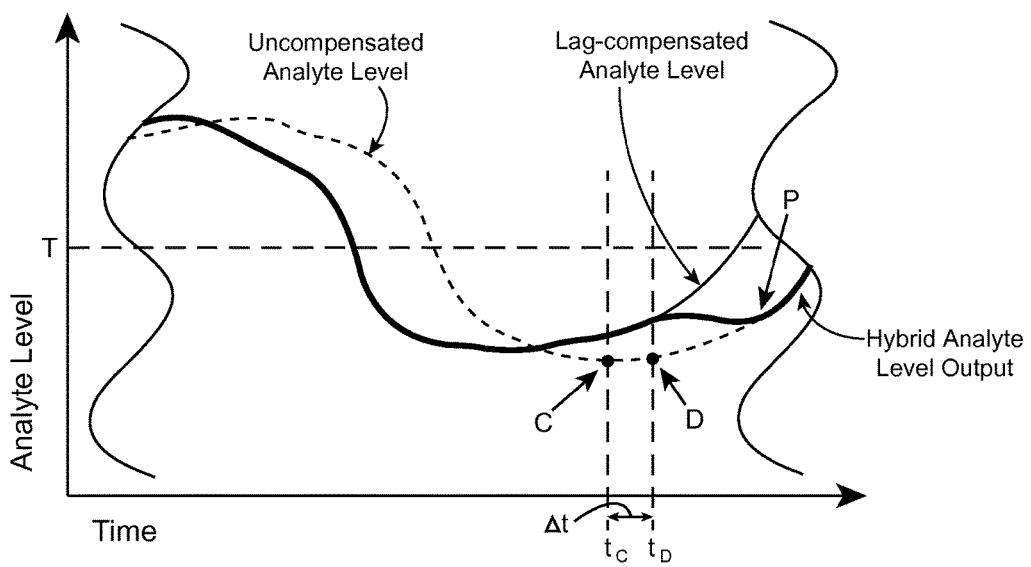
FIG. 7B illustrates a chart of a hybrid output as it transitions from lag-compensated analyte levels to uncompensated analyte levels, according to one embodiment.

FIG. 7B illustrates a chart of a hybrid output as it transitions from lag-compensated analyte levels to uncompensated analyte levels, according to one embodiment. The example embodiment shown in FIG. 7B differs from the example embodiment shown in FIG. 7A by having a smoothing function implemented for the transition. For the sake of brevity and clarity, only the transition period is discussed for FIG. 7B.

As similarly described above for FIG. 7A, at point D, the uncompensated analyte level (and thus selected analyte level) is below the threshold value and has been rising for the predetermined duration of time (e.g., Δt). Thus, the criteria is now met for the hybrid output to stop tracking the lag-compensated analyte levels and to start tracking the uncompensated analyte levels. Since the hybrid output is transitioning, a smoothing function is applied to provide a smooth transition from the lag-compensated analyte levels to uncompensated analyte levels. For example, the smoothing function may include weighted combinations of lag-compensated and uncompensated analyte levels that vary over the transition period. At point P, the hybrid output has completely transitioned to the uncompensated analyte levels and the smoothing function is no longer applied.

Figure 8A:
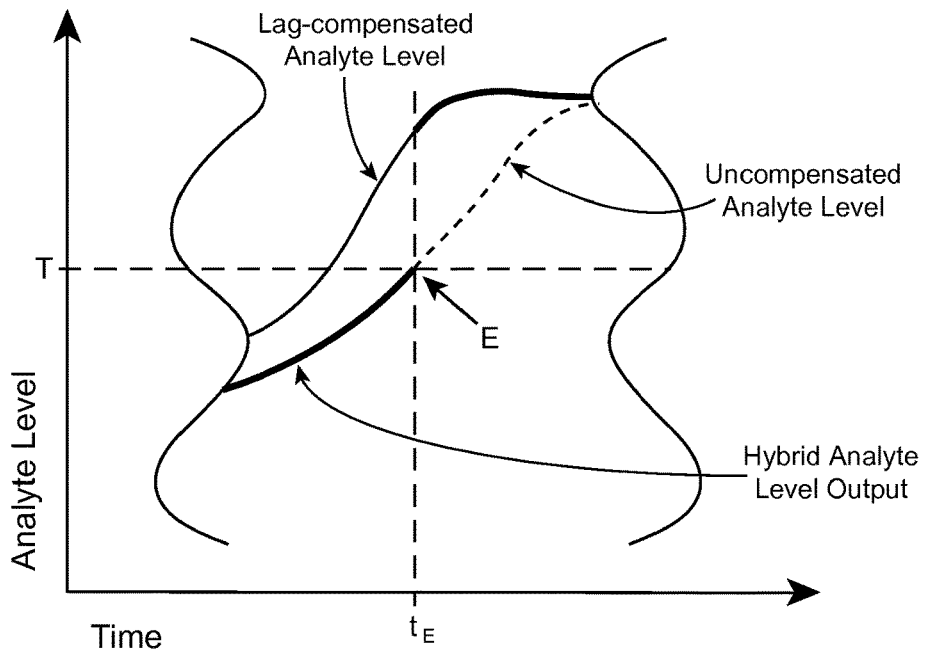
FIG. 8A illustrates a chart of a hybrid output as it transitions from uncompensated analyte levels to lag-compensated analyte levels, according to one embodiment.

FIG. 8A illustrates a chart of a hybrid output as it transitions from uncompensated analyte levels to lag-compensated analyte levels, according to one embodiment. For the exemplary embodiment shown, the predetermined criteria includes criteria for continuing to track the uncompensated analyte levels until the selected analyte level is either not below the threshold value T or has not rising for a predetermined duration of time. In another embodiment, the criteria for having not been rising for a predetermined duration of time may instead be "beginning to decline for a predetermined duration of time".

In the embodiment shown, the graph begins with the hybrid output tracking the uncompensated analyte level, and the most recently calculated uncompensated analyte level is used as the selected analyte level for comparison to the predetermined criteria. The uncompensated analyte level (and thus selected analyte level) is shown at the start of the graph as being below the predetermined threshold. Furthermore, the uncompensated analyte level (and thus selected analyte level) is trending upward. Thus, the criteria for tracking the uncompensated analyte level is still met. If for example, the uncompensated analyte level was below the threshold value but began to trend downward (not shown in FIG. 8A), then the criteria would not be met for tracking the uncompensated analyte level and the hybrid output would begin tracking the lag-compensated analyte level.

At point E, the uncompensated analyte level (and thus selected analyte level) is no longer below the threshold line T, and thus the criteria for tracking the uncompensated analyte level is no longer met. As shown in the graph, the hybrid output begins tracking the lag-compensated analyte levels at time $t_E$. In the embodiment shown, no smoothing function is implemented and thus the hybrid output jumps from the uncompensated analyte levels to the lag-compensated analyte levels.

After the hybrid output tracks the lag-compensated analyte levels, a selected analyte level is compared to the predetermined criteria to determine when to stop tracking the lag-compensated analyte levels and to start tracking the uncompensated analyte levels again. The selected analyte level may or may not be derived from the same source after the transition. For example, in one embodiment, the most recently calculated uncompensated analyte level continues to be used as the selected analyte level that is compared to the predetermined criteria. In another embodiment, for example, the most recently generated lag-compensated analyte level (or the most recently generated hybrid output) is then used as the selected analyte level that is compared to the predetermined criteria.

Figure 8B:
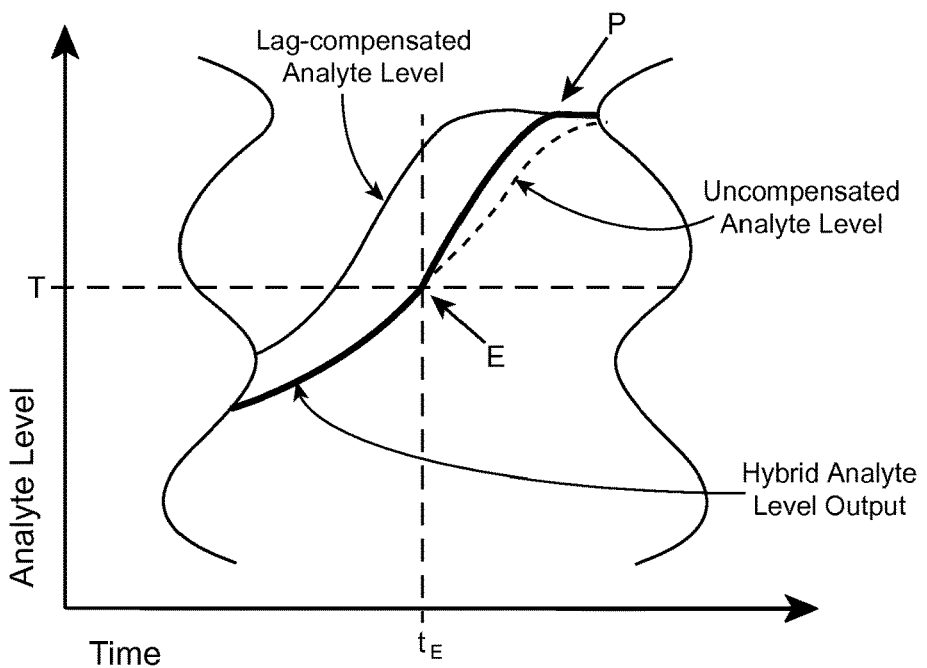
FIG. 8B illustrates a chart of a hybrid output as it transitions from uncompensated analyte levels to lag-compensated analyte levels, according to one embodiment.

FIG. 8B illustrates a chart of a hybrid output as it transitions from uncompensated analyte levels to lag-compensated analyte levels, according to one embodiment. The example embodiment shown in FIG. 8B differs from the example embodiment shown in FIG. 8A by having a smoothing function implemented for the transition. For the sake of brevity and clarity, only the transition period is discussed for FIG. 8B.

As similarly described above for FIG. 8A, at point E, the uncompensated analyte level (and thus selected analyte level) is no longer below the threshold value. Thus, the criteria is now met for the hybrid output to stop tracking the uncompensated analyte levels and to start tracking the lag-compensated analyte levels. Since the hybrid output is transitioning, a smoothing function is applied to provide a smooth transition from the uncompensated analyte levels to lag-compensated analyte levels. For example, the smoothing function may include weighted combinations of lag-compensated and uncompensated analyte levels that vary over the transition period. At point P, the hybrid output has completely transitioned to the lag-compensated analyte levels and the smoothing function is no longer applied.

Figure 9A:
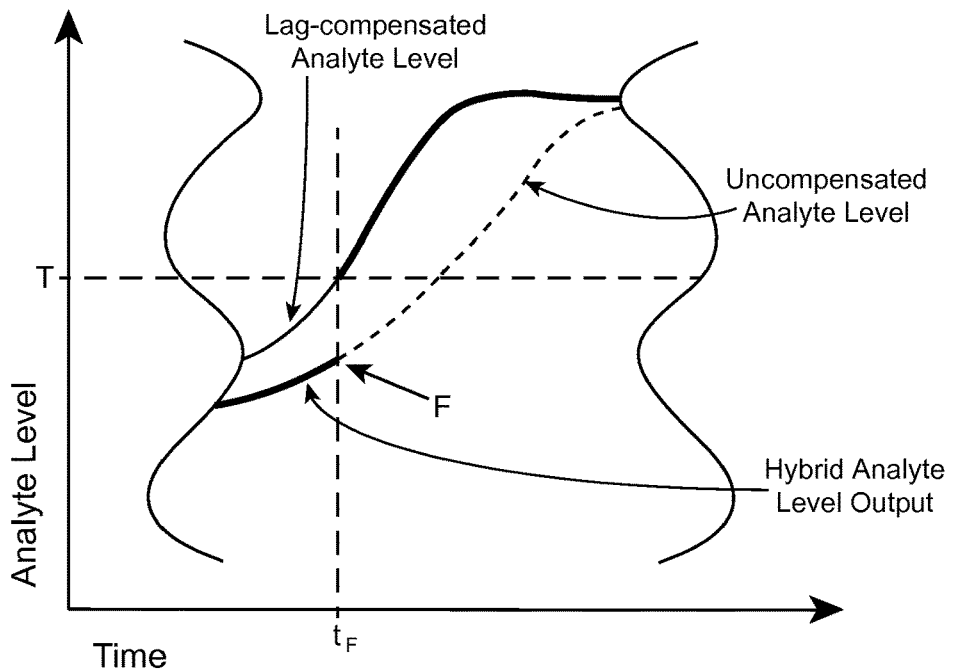
FIG. 9A illustrates a chart of a hybrid output as it transitions from uncompensated analyte levels to lag-compensated analyte levels, according to one embodiment.

FIG. 9A illustrates a chart of a hybrid output as it transitions from uncompensated analyte levels to lag-compensated analyte levels, according to one embodiment. For the exemplary embodiment shown, the predetermined criteria includes criteria for continuing to track the uncompensated analyte levels until the selected analyte level is either not below the threshold value T or has not rising for a predetermined duration of time.

In the embodiment shown, the graph begins with the hybrid output tracking the uncompensated analyte level, and the most recently calculated lag-compensated analyte level is used as the selected analyte level for comparison to the predetermined criteria. The lag-compensated analyte level (and thus selected analyte level) is shown at the start of the graph to be below the predetermined threshold. Furthermore, the lag-compensated analyte level (and thus selected analyte level) is trending upward. Thus, the criteria for tracking the uncompensated analyte level is still met. If, for example, the lag-compensated analyte level was below the threshold value but began to trend downward (not shown in FIG. 9A), then the criteria would not be met for tracking the uncompensated analyte level and the hybrid output would begin tracking the lag-compensated analyte level.

At point F, the lag-compensated analyte level (and thus selected analyte level) is no longer below the threshold line T, and thus the criteria for tracking the uncompensated analyte level is no longer met. As shown in the graph, the hybrid output begins tracking the lag-compensated analyte levels at time $t_F$. In the embodiment shown, no smoothing function is implemented and thus the hybrid output jumps from the uncompensated analyte levels to the lag-compensated analyte levels.

After the hybrid output begins tracking the lag-compensated analyte levels, a selected analyte level is compared to the predetermined criteria to determine when to stop tracking the lag-compensated analyte levels and to start tracking the uncompensated analyte levels again. The selected analyte level may or may not be derived from the same source after the transition. For example, in one embodiment, the most recently generated lag-compensated analyte level continues to be used as the selected analyte level that is compared to the predetermined criteria. In another embodiment, for example, the most recently calculated uncompensated analyte level (or the most recently generated hybrid output) is now used as the selected analyte level that is compared to the predetermined criteria.

Figure 9B:
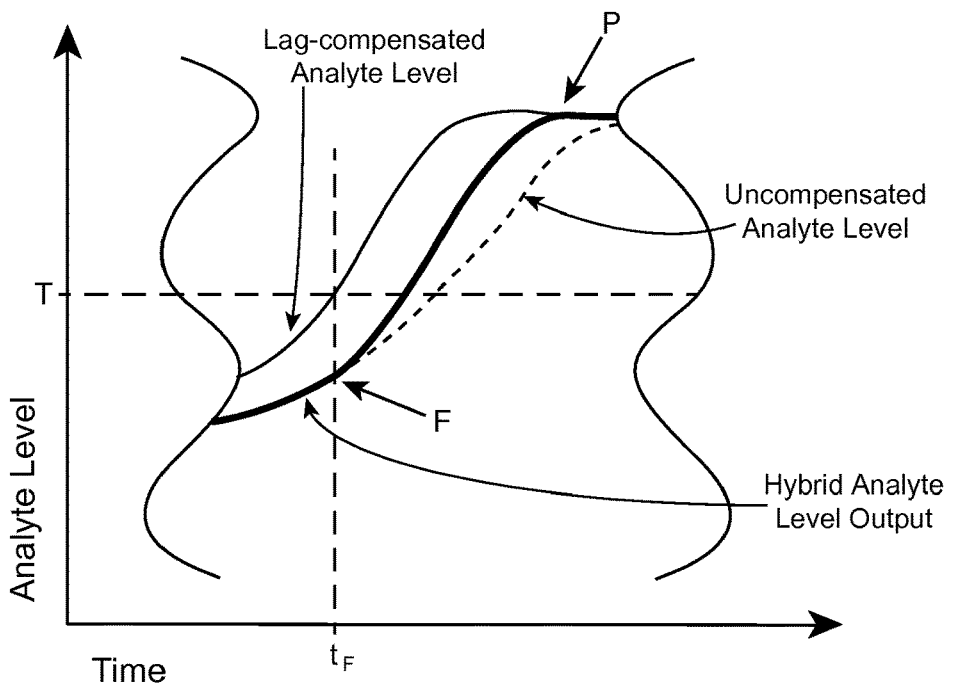
FIG. 9B illustrates a chart of a hybrid output as it transitions from uncompensated analyte levels to lag-compensated analyte levels, according to one embodiment.

FIG. 9B illustrates a chart of a hybrid output as it transitions from uncompensated analyte levels to lag-compensated analyte levels, according to one embodiment. The example embodiment shown in FIG. 9B differs from the example embodiment shown in FIG. 9A by having a smoothing function implemented for the transition. For the sake of brevity and clarity, only the transition period is discussed for FIG. 9B.

As similarly described above for FIG. 9A, at point F, the lag-compensated analyte level (and thus selected analyte level) is no longer below the threshold value T. Thus, the criteria is now met for the hybrid output to stop tracking the uncompensated analyte levels and to start tracking the lag-compensated analyte levels. Since the hybrid output is transitioning, a smoothing function is applied to provide a smooth transition from the uncompensated analyte levels to lag-compensated analyte levels. For example, the smoothing function may include weighted combinations of lag-compensated and uncompensated analyte levels that vary over the transition period. At point P, the hybrid output has completely transitioned to the lag-compensated analyte levels and the smoothing function is no longer applied.

Figure 10:
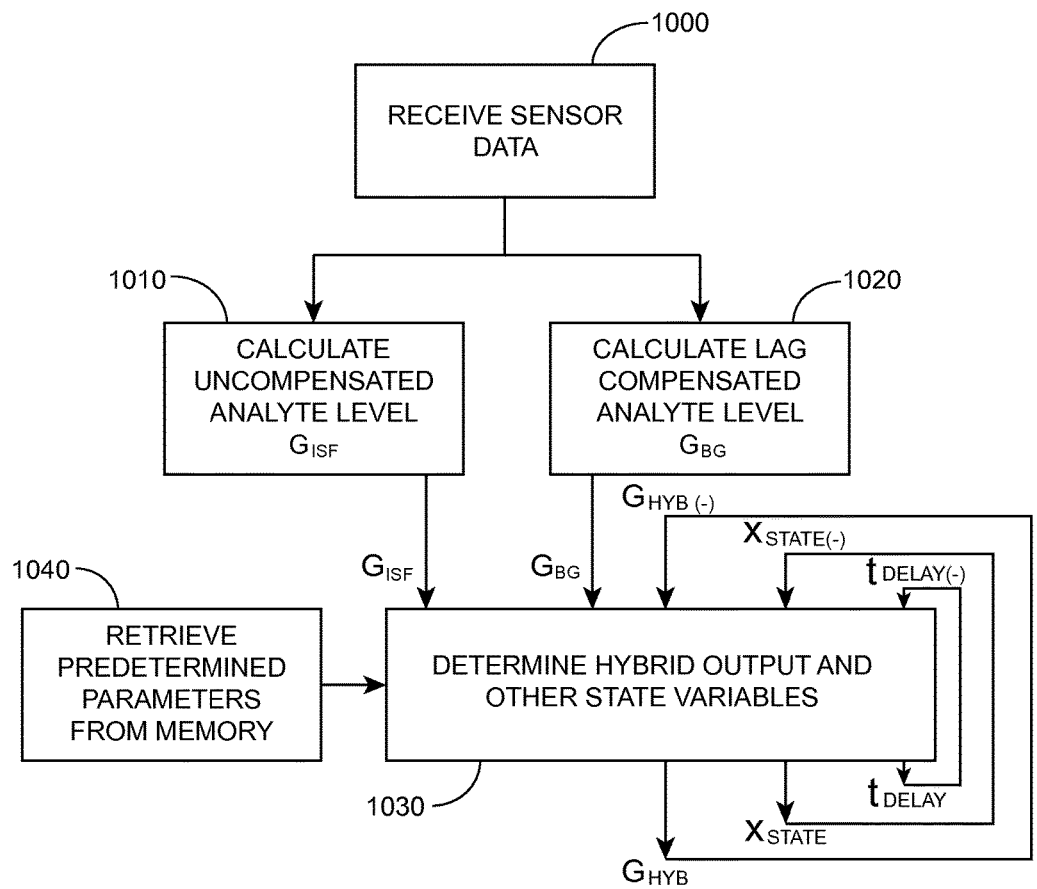
FIG. 10 illustrates a flowchart for a method of generating a hybrid analyte level output, according to one embodiment.

FIG. 10 illustrates a flowchart for a method of generating a hybrid analyte level output, according to one embodiment. In some instances, such as with CGM systems and intermittent or periodic interrogation analyte sensing systems, sensor data continues to be received over time.

In the embodiment illustrated in FIG. 10, the analyte (or sensor) data are received periodically at 1000. This sensor data may be "raw", meaning that it would need to be processed to represent the analyte level. For instance, the raw sensor data may need to be multiplied by a conversion factor to represent an analyte level. Furthermore, an analyte level may be determined, sometimes in the form of a filter, from the most recently received sensor data in conjunction with one or more historical sensor data retrieved from memory. These and other forms of processing raw sensor data to determine an analyte level are well known in the art.

Two analyte levels (e.g., glucose levels) are determined by processing the raw data, as illustrated in FIG. 10. At 1010, uncompensated analyte levels, termed as $G_{ISF}$, are determined for each sensor data received which represent, for instance, ISF glucose levels. At 1020, compensated analyte levels, termed as $G_{BG}$, are determined for each sensor data received which represent, for instance, blood glucose (BG) levels. The BG levels may be distinct from the ISF levels, in that the BG levels have been corrected for lag, using lag correction techniques that are well known in the art.

The hybrid output analyte level output, $G_{HYB}$, is determined by the predetermined criteria in process in 1030. This process is executed for every received sensor data. Inputs to the process are the compensated and uncompensated levels, predetermined parameters retrieved from memory (1040), for example, in this embodiment, a threshold parameter, $G_{LOW}$, and a transition-smoothing time-constant parameter, $\tau$. The process also has inputs in the form of feedback from the output of the process at its prior executions; these variables, $x_{STATE}$ and $t_{DECAY}$, along with $\tau$, are used to manage the transition smoothing. For this embodiment, there are three possible values for $x_{STATE}$; "use $G_{BG}$", "use minimum" or "use transition". $\tau$ is a constant, such as 10; for sensor received every minute, $\tau$ would equal 10 minutes. The variable $t_{DECAY}$ will vary from 0 to $\tau$, as incremented by the process 1030. Finally, the hybrid signal itself is a state variable fed back into the process 1030.

The description of the process 1030 can be described by pseudo-code given below. The initial state is set to $G_{HYB}=G_{BG}$, $x_{STATE}$="use $G_{BG}$" and $t_{DECAY}=0$. The hybrid output will be determined according to the predetermined criteria based on the two level inputs as described in the logic below:

If $(G_{HYB}(-)>G_{LOW})$AND$(x_{STATE}(-)=$"use $G_{BG}$"), then
  $G_{HYB}=G_{BG}$, $x_{STATE}=$"use $G_{BG}$", and $t_{DECAY}=0$;

If $(G_{HYB}(-)<=G_{LOW})$, then $G_{HYB}=$minimum$(G_{BG}, G_{ISF})$, $x_{STATE}=$"use minimum", and $t_{DECAY}=0$;

If $(G_{HYB}(-)>G_{LOW})$AND$(x_{STATE}(-)=$"use minimum"), then $G_{HYB}=$minimum$(G_{BG}, G_{ISF})$, $x_{STATE}=$"use transition", and $t_{DECAY}=1$;

If $(G_{HYB}(-)>G_{LOW})$AND$(x_{STATE}(-)=$"use transition") AND$(t_{DECAY}(-)<\tau)$, then $G_{HYB}=((\tau-t_{DECAY})/\tau)$ *minimum$(G_{BG},G_{ISF})+(t_{DECAY}/\tau)*G_{BG}$, $x_{STATE}=$"use transition", and $t_{DECAY}=t_{DECAY}(-)+1$;

If $(G_{HYB}(-)>G_{LOW})$AND$(x_{STATE}(-)=$"use transition") AND$(t_{DECAY}(-)=\tau)$, then $G_{HYB}=G_{BG}$, $x_{STATE}=$"use $G_{BG}$", and $t_{DECAY}=0$;

where the symbol "(-)" denotes a state variable value from the previous process execution, and variables without this symbol are assumed to be for the present execution.

The logic describe above provides a process where the hybrid level reflects the blood glucose level until it transitions below the low glucose threshold, where it reflects the lower of the blood glucose or ISF glucose level. When the hybrid output rises above the low glucose threshold, the last three logical statements provide a state machine that smoothly transitions the hybrid signal from this minimum level to the blood glucose level. This function will behave similarly as illustrated in FIG. 3. In addition, when the hybrid level falls below the low glucose threshold before a transition has completed (that is, when $0<(t_{DECAY}(-)<\tau)$, the behavior of this logic is acceptable in that the hybrid output would return to the lower of the two input levels, as directed by the second logic statement.

The hybrid output, $G_{HYB}$, may be used the same as any analyte level is commonly used in a system. For instance, glucose levels determined by a CGM system are commonly used in display to the patient or care giver, in logging in memory for future upload and analysis, and in monitoring by alarm monitoring functions. The hybrid output would be used in the same way. As mentioned, one advantage of the hybrid output is in its use for alarm monitoring and display, such that the BG level provides prompt warning of low blood glucose levels to the patient, while the ISF glucose level provides a conservative measure of lingering low ISF glucose while the blood glucose is rising.

Variations of this embodiment should be readily apparent. For instance, the processes may be run at frequencies different from the frequency of received sensor data, such as every other received data or every fifth received data. Also, this invention may be generalized to combine more than two levels according to a predetermined criterion. In addition, this invention may be generalized to include two or more constant thresholds as parameters in the predetermined criterion for determining a hybrid level; for instance, one threshold may be used for switching the hybrid level to the minimum of the BG or ISF levels, and another threshold may be used for switching the hybrid level back to transitioning to the BG level. In addition, the predetermined parameters may have different values that may be set by the operator or set by some other condition automatically detected by this system or another system. Also, the predetermined criterion for generating the hybrid level may incorporate more complicated or advanced forms of filtering or smoothing than what is described here.

Devices and Systems

Embodiments of the present disclosure relate to methods, devices, and systems for detecting at least one analyte, including glucose, in body fluid. Embodiments relate to the continuous, periodic, and intermitted) in vivo monitoring of the level of one or more analytes using a continuous or on-demand analyte monitoring device or system. The system may include an analyte sensor at least a portion of which is to be positioned beneath a skin surface of a user for a period of time. The present disclosure may also be applicable to discrete monitoring of one or more analytes using an in vitro blood glucose ("BG") meter and an analyte test strip.

Embodiments include combined or combinable devices, systems and methods and/or transferring data between an in vivo continuous system and an in vivo system. In one embodiment, the systems, or at least a portion of the systems, are integrated into a single unit.

For example, the analyte monitoring devices and systems may include, or communicate with, an analyte sensor at least a portion of which is positionable beneath the skin surface of the user for the in vivo detection of an analyte, including glucose, lactate, and the like, in a body fluid. Embodiments include wholly implantable analyte sensors and analyte sensors in which only a portion of the sensor is positioned under the skin and a portion of the sensor resides above the skin, e.g., for contact to a sensor control unit (which may include a communication module, e.g., a transmitter or the like), a receiver/display unit, transceiver, processor, etc. The sensor may be, for example, subcutaneously positionable in a user for the continuous, periodic, or on-demand monitoring of a level of an analyte in the user's interstitial fluid.

In one embodiment, an analyte sensor may be positioned in contact with interstitial fluid to detect the level of glucose, which detected glucose may be used to infer the glucose level in the user's bloodstream. Embodiments of the analyte sensors may be configured for monitoring the level of the analyte over a time period which may range from seconds, minutes, hours, days, weeks, to months, or longer.

In one embodiment, the analyte sensors, such as glucose sensors, are capable of in vivo detection of an analyte for one hour or more, e.g., a few hours or more, e.g., a few days or more, e.g., three or more days, e.g., five days or more, e.g., seven days or more, e.g., several weeks or more, or one month or more.

As demonstrated herein, the methods of the present disclosure are useful in connection with a device that is used to measure or monitor an analyte (e.g., glucose), such as any such device described herein. These methods may also be used in connection with a device that is used to measure or monitor another analyte (e.g., ketones, ketone bodies, HbA1c, and the like), including oxygen, carbon dioxide, proteins, drugs, or another moiety of interest, for example, or any combination thereof, found in bodily fluid, including subcutaneous fluid, dermal fluid (sweat, tears, and the like), interstitial fluid, or other bodily fluid of interest, for example, or any combination thereof.

Figure 11:
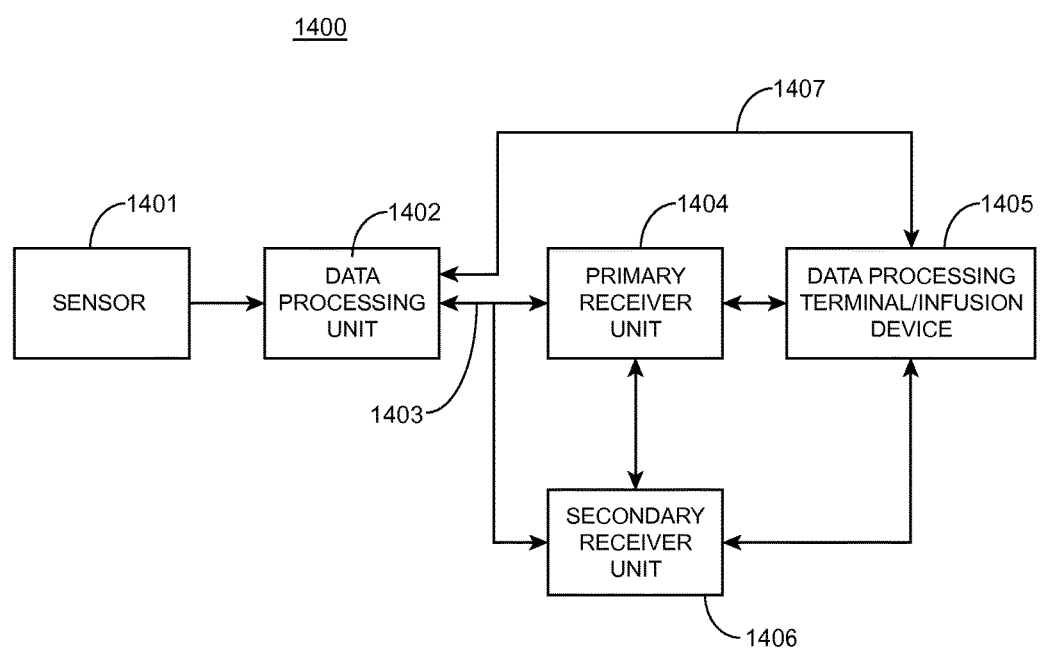
FIG. 11 shows an analyte monitoring system, according to one embodiment.

FIG. 11 shows an analyte (e.g., glucose) monitoring system, according to one embodiment. Aspects of the subject disclosure are further described primarily with respect to glucose monitoring devices and systems, and methods of glucose detection, for convenience only and such description is in no way intended to limit the scope of the embodiments. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

The analyte monitoring system 1400 includes an analyte sensor 1401, a data processing unit 1402 connectable to the sensor 1401, and a primary receiver unit 1404. In some instances, the primary receiver unit 1404 is configured to communicate with the data processing unit 1402 via a communication link 1403. In one embodiment, the primary receiver unit 1404 may be further configured to transmit data to a data processing terminal 1405 to evaluate or otherwise process or format data received by the primary receiver unit 1404. The data processing terminal 1405 may be configured to receive data directly from the data processing unit 1402 via a communication link 1407, which may optionally be configured for bi-directional communication. Further, the data processing unit 1402 may include a transmitter or a transceiver to transmit and/or receive data to and/or from the primary receiver unit 1404 and/or the data processing terminal 1405 and/or optionally a secondary receiver unit 1406.

Also shown in FIG. 11 is an optional secondary receiver unit 1406 which is operatively coupled to the communication link 1403 and configured to receive data transmitted from the data processing unit 1402. The secondary receiver unit 1406 may be configured to communicate with the primary receiver unit 1404, as well as the data processing terminal 1405. In one embodiment, the secondary receiver unit 1406 may be configured for bi-directional wireless communication with each of the primary receiver unit 1404 and the data processing terminal 1405. As discussed in further detail below, in some instances, the secondary receiver unit 1406 may be a de-featured receiver as compared to the primary receiver unit 1404, for instance, the secondary receiver unit 1406 may include a limited or minimal number of functions and features as compared with the primary receiver unit 1404. As such, the secondary receiver unit 1406 may include a smaller (in one or more, including all, dimensions), compact housing or embodied in a device including a wrist watch, arm band, PDA, mp3 player, cell phone, etc., for example. Alternatively, the secondary receiver unit 106 may be configured with the same or substantially similar functions and features as the primary receiver unit 1404. The secondary receiver unit 106 may include a docking portion configured to mate with a docking cradle unit for placement by, e.g., the bedside for night time monitoring, and/or a bi-directional communication device. A docking cradle may recharge a power supply.

Only one analyte sensor 1401, data processing unit 1402 and data processing terminal 1405 are shown in the embodiment of the analyte monitoring system 1400 illustrated in FIG. 11. However, the analyte monitoring system 1400 may include more than one sensor 1401 and/or more than one data processing unit 1402, and/or more than one data processing terminal 1405. Multiple sensors may be positioned in a user for analyte monitoring at the same or different times.

The analyte monitoring system 1400 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 1400. For example, unique IDs, communication channels, and the like, may be used.

In one embodiment, the sensor 1401 is physically positioned in or on the body of a user whose analyte level is being monitored. The sensor 1401 may be configured to at least periodically sample the analyte level of the user and convert the sampled analyte level into a corresponding signal for transmission by the data processing unit 1402. The data processing unit 1402 is coupleable to the sensor 1401 so that both devices are positioned in or on the user's body, with at least a portion of the analyte sensor 1401 positioned transcutaneously. The data processing unit may include a fixation element, such as an adhesive or the like, to secure it to the user's body. A mount (not shown) attachable to the user and mateable with the data processing unit 1402 may be used. For example, a mount may include an adhesive surface. The data processing unit 1402 performs data processing functions, where such functions may include, but are not limited to, filtering and encoding of data signals, each of which corresponds to a sampled analyte level of the user, for transmission to the primary receiver unit 1404 via the communication link 1403. In one embodiment, the sensor 1401 or the data processing unit 1402 or a combined sensor/data processing unit may be wholly implantable under the skin surface of the user.

In one embodiment, the primary receiver unit 1404 may include an analog interface section including an RF receiver and an antenna that is configured to communicate with the data processing unit 1402 via the communication link 1403, and a data processing section for processing the received data from the data processing unit 1402 including data decoding, error detection and correction, data clock generation, data bit recovery, etc., or any combination thereof.

In operation, the primary receiver unit 1404 in one embodiment is configured to synchronize with the data processing unit 1402 to uniquely identify the data processing unit 1402, based on, for example, an identification information of the data processing unit 1402, and thereafter, to periodically receive signals transmitted from the data processing unit 1402 associated with the monitored analyte levels detected by the sensor 1401.

Referring again to FIG. 11, the data processing terminal 1405 may include a personal computer, a portable computer including a laptop or a handheld device such as a consumer electronics device (e.g., a personal digital assistant (PDA), a telephone including a cellular phone (e.g., a multimedia and Internet-enabled mobile phone including an iPhone™, a Blackberry®, or similar phone), an mp3 player (e.g., an iPOD™, etc.), a pager, and the like), and/or a drug delivery device (e.g., an infusion device), each of which may be configured for data communication with the receiver via a wired or a wireless connection. Additionally, the data processing terminal 1405 may further be connected to a data network (not shown) for storing, retrieving, updating, and/or analyzing data corresponding to the detected analyte level of the user.

The data processing terminal 1405 may include a drug delivery device (e.g., an infusion device) such as an insulin infusion pump or the like, which may be configured to administer a drug (e.g., insulin) to the user, and which may be configured to communicate with the primary receiver unit 104 for receiving, among others, the measured analyte level. Alternatively, the primary receiver unit 1404 may be configured to integrate an infusion device therein so that the primary receiver unit 1404 is configured to administer an appropriate drug (e.g., insulin) to users, for example, for administering and modifying basal profiles, as well as for determining appropriate boluses for administration based on, among others, the detected analyte levels received from the data processing unit 1402. An infusion device may be an external device or an internal device, such as a device wholly implantable in a user.

In one embodiment, the data processing terminal 1405, which may include an infusion device, e.g., an insulin pump, may be configured to receive the analyte signals from the data processing unit 1402, and thus, incorporate the functions of the primary receiver unit 1404 including data processing for managing the user's insulin therapy and analyte monitoring. In one embodiment, the communication link 1403, as well as one or more of the other communication interfaces shown in FIG. 11, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

Figure 12:
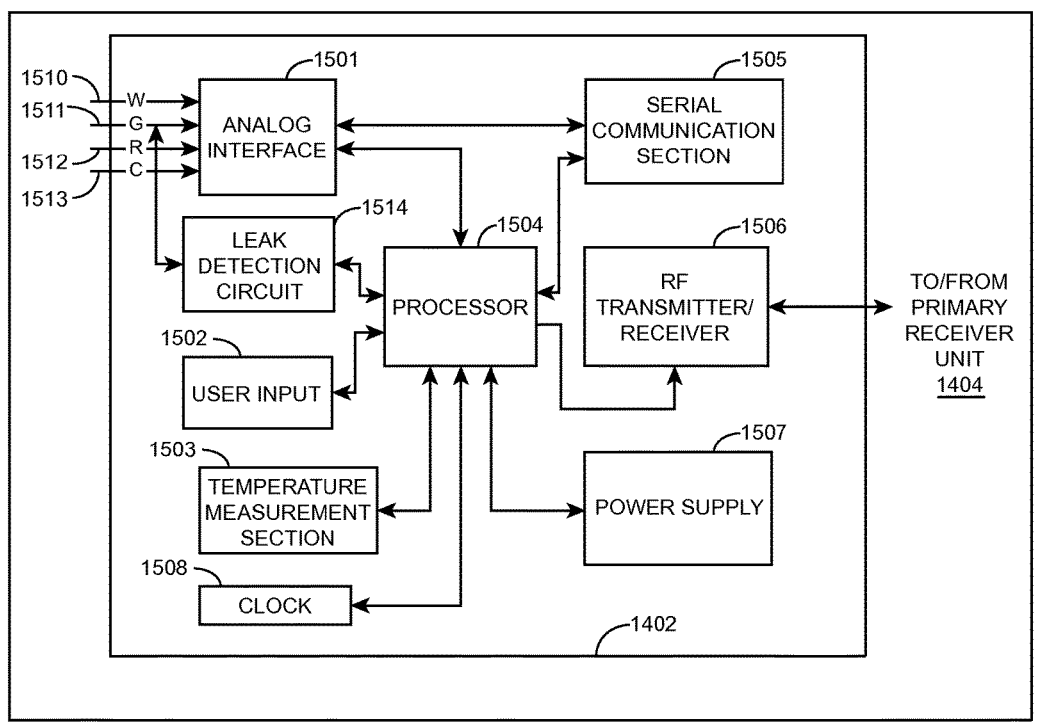
FIG. 12 is a block diagram of the data processing unit shown in FIG. 11, according to one embodiment.

FIG. 12 is a block diagram of the data processing unit 1402 shown in FIG. 11 in accordance with one embodiment. Data processing unit 1402 includes an analog interface 1501 configured to communicate with the sensor 1401 (FIG. 1), a user input 1502, and a temperature measurement section 1503, each of which is operatively coupled to processor 1504 such as a central processing unit (CPU). Furthermore, unit 1402 is shown to include a serial communication section 1505, clock 1508, and an RF transmitter 1506, each of which is also operatively coupled to the processor 1504. Moreover, a power supply 1507 such as a battery is also provided in unit 1402 to provide the necessary power.

In another embodiment, the data processing unit may not include all components in the exemplary embodiment shown. User input and/or interface components may be included or a data processing unit may be free of user input and/or interface components. In one embodiment, one or more application-specific integrated circuits (ASIC) may be used to implement one or more functions or routines associated with the operations of the data processing unit (and/or receiver unit) using for example one or more state machines and buffers.

As can be seen in the embodiment of FIG. 12, the analyte sensor 1401 (FIG. 1) includes four contacts, three of which are electrodes: a work electrode (W) 1510, a reference electrode (R) 1512, and a counter electrode (C) 1513, each operatively coupled to the analog interface 1501 of the data processing unit 1402. This embodiment also shows an optional guard contact (G) 1511. Fewer or greater electrodes may be employed. For example, the counter and reference electrode functions may be served by a single counter/ reference electrode. In some cases, there may be more than one working electrode and/or reference electrode and/or counter electrode, etc.

Figure 13:
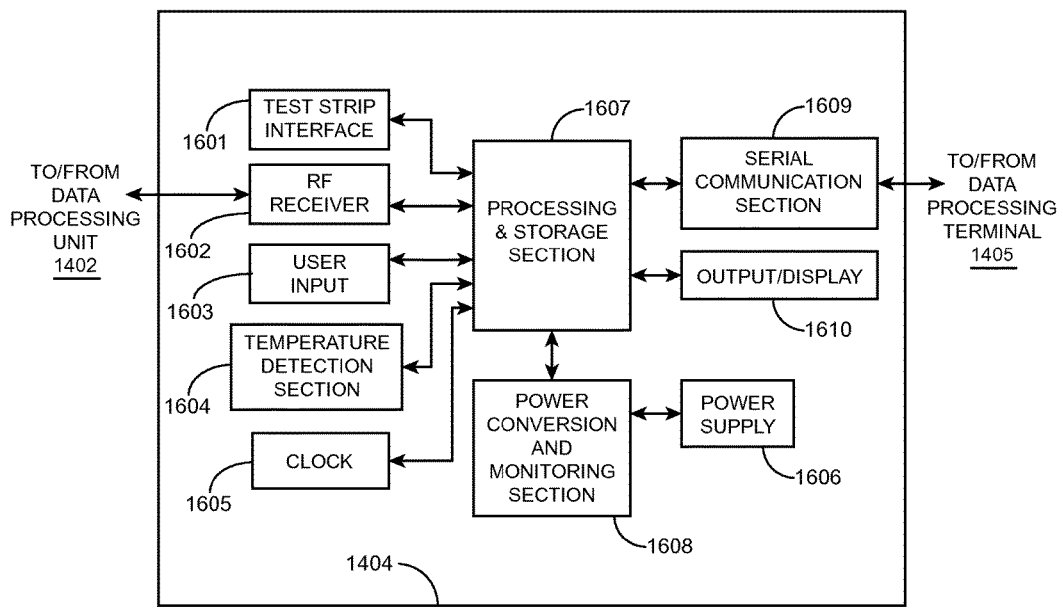
FIG. 13 is a block diagram of an embodiment of a receiver/monitor unit such as the primary receiver unit of the analyte monitoring system shown in FIG. 11, according to one embodiment.

FIG. 13 is a block diagram of an embodiment of a receiver/monitor unit such as the primary receiver unit 1404 of the analyte monitoring system shown in FIG. 11. The primary receiver unit 1404 includes one or more of: a test strip interface 1601, an RF receiver 1602, a user input 1603, an optional temperature detection section 1604, and a clock 1605, each of which is operatively coupled to a processing and storage section 1607. The primary receiver unit 1404 also includes a power supply 1606 operatively coupled to a power conversion and monitoring section 1608. Further, the power conversion and monitoring section 1608 is also coupled to the processing and storage section 1607. Moreover, also shown are a receiver serial communication section 1609, and an output 1610, each operatively coupled to the processing and storage section 1607. The primary receiver unit 1404 may include user input and/or interface components or may be free of user input and/or interface components.

In one embodiment, the test strip interface 1601 includes an analyte testing portion (e.g., a glucose level testing portion) to receive a blood (or other body fluid sample) analyte test or information related thereto. For example, the test strip interface 1601 may include a test strip port to receive a test strip (e.g., a glucose test strip). The device may determine the analyte level of the test strip, and optionally display (or otherwise notice) the analyte level on the output 1610 of the primary receiver unit 1404. Any suitable test strip may be employed, e.g., test strips that only require a very small amount (e.g., 3 microliters or less, e.g., 1 microliter or less, e.g., 0.5 microliters or less, e.g., 0.1 microliters or less), of applied sample to the strip in order to obtain accurate glucose information. Embodiments of test strips include, e.g., Freestyle® and Precision® blood glucose test strips from Abbott Diabetes Care, Inc. (Alameda, Calif.). Glucose information obtained by an in vitro glucose testing device may be used for a variety of purposes, computations, etc. For example, the information may be used to calibrate sensor 1401, confirm results of sensor 1401 to increase the confidence thereof (e.g., in instances in which information obtained by sensor 1401 is employed in therapy related decisions), etc.

In further embodiments, the data processing unit 1402 and/or the primary receiver unit 1404 and/or the secondary receiver unit 1406, and/or the data processing terminal/infusion device 1405 may be configured to receive the analyte value wirelessly over a communication link from, for example, a blood glucose meter. In further embodiments, a user manipulating or using the analyte monitoring system 1400 (FIG. 11) may manually input the analyte value using, for example, a user interface (for example, a keyboard, keypad, voice commands, and the like) incorporated in one or more of the data processing unit 1402, the primary receiver unit 1404, secondary receiver unit 1406, or the data processing terminal/infusion device 1405.

The features and techniques described in the present disclosure may be performed, for example, by the processing circuitry within the data processing unit 1402 or receiving unit 1404, or combination of both.

Additional detailed descriptions are provided in U.S. Pat. Nos. 5,262,035; 5,264,104; 5,262,305; 5,320,715; 5,593,852; 6,175,752; 6,650,471; 6,746,582, and 7,811,231, each of which is incorporated herein by reference in their entirety.

In one embodiment of the present disclosure, the analyte monitoring device includes processing circuitry that is able to determine a level of the analyte and activate an alarm system if the analyte level exceeds a threshold. The analyte monitoring device, in these embodiments, has an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the user has entered a hyperglycemic state. As another example, a datapoint which correlates to a glucose level of 65 mg/dL exceeds a threshold value for hypoglycemia of 70 mg/dL because the datapoint indicates that the user is hypoglycemic as defined by the threshold value. However, a datapoint which correlates to a glucose level of 75 mg/dL would not exceed the same threshold value for hypoglycemia because the datapoint does not indicate that particular condition as defined by the chosen threshold value.

An alarm may also be activated if the sensor readings indicate a value that is beyond a measurement range of the sensor. For glucose, the physiologically relevant measurement range may be 30-400 mg/dL, including 40-300 mg/dL and 50-250 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system might be activated if the rate of change in glucose concentration exceeds a threshold value which might indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The present disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Each of the various references, presentations, publications, provisional and/or non-provisional U.S. patent applications, U.S. patents, non-U.S. Patent Applications, and/or non-U.S. Patents that have been identified herein, is incorporated herein by reference in its entirety.

Other embodiments and modifications within the scope of the present disclosure will be apparent to those skilled in the relevant art. Various modifications, processes, as well as numerous structures to which the embodiments of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example. Although various aspects and features of the present disclosure may have been described largely with respect to applications, or more specifically, medical applications, involving diabetic humans, it will be understood that such aspects and features also relate to any of a variety of applications involving non-diabetic humans and any and all other animals. Further, although various aspects and features of the present disclosure may have been described largely with respect to applications involving partially in vivo positioned sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the present disclosure have been described with respect to various embodiments and specific examples herein, all of which may be made or carried out conventionally, it will be understood that the invention is entitled to protection within the full scope of the appended claims.

Example Embodiments

Example embodiments are provided below. The embodiments are exemplary and not intended to be limiting. Other embodiments or variations may also be within the scope of the present disclosure.

In some aspects, methods of generating a hybrid analyte level output are provided. The methods include receiving sensor data; and generating a hybrid analyte level output including uncompensated analyte levels and lag-compensated analyte levels, wherein the uncompensated analyte levels lag in time with respect to the lag-compensated analyte levels. The hybrid analyte level output tracks between the uncompensated analyte levels and the lag-compensated analyte levels according to predetermined criteria.

In certain embodiments, the predetermined criteria includes criteria for tracking the uncompensated analyte levels when selected analyte levels are below a predetermined threshold and have been rising for at least a predetermined duration of time; and criteria for tracking the lag-compensated levels when the selected analyte levels are not below the predetermined threshold or have not been rising for at least the predetermined duration of time.

In certain embodiments, the predetermined criteria includes criteria for continuing to track the lag-compensated analyte levels until selected analyte levels are below a predetermined threshold and have been rising for at least a predetermined duration of time. In certain embodiments, the predetermined criteria includes criteria for continuing to track the uncompensated analyte levels until selected analyte levels are not below a predetermined threshold or have not been rising for at least a predetermined duration of time. In certain instances, the predetermined threshold related to tracking the lag-compensated analyte levels may be the same as the predetermined threshold related to the tracking the uncompensated analyte levels in one embodiment, but different in another embodiment. Similarly, in certain instances, the predetermined duration of time related to tracking the lag-compensated analyte levels may be the same as the predetermined duration of time related to the tracking the uncompensated analyte levels in one embodiment, but different in another embodiment.

In certain embodiments, the predetermined criteria includes criteria for continuing to track the uncompensated analyte levels until selected analyte levels are not below a first predetermined threshold or have not been rising for at least a first predetermined duration of time. The selected analyte levels may vary in different embodiments. For example, in one embodiment, the selected analyte levels may include the most recently generated lag-compensated analyte levels. In another embodiment, the selected analyte levels may include the most recently calculated uncompensated analyte levels. In yet another embodiment, the selected analyte levels may include the most recently generated hybrid analyte level outputs. In some embodiment, the selected analyte levels may include one or more of the preceding sources—e.g., the most recently generated lag-compensated analyte levels, the most recently calculated uncompensated analyte levels, and the most recently generated hybrid analyte level outputs. For instance, various times, conditions, events, etc., may be predetermined and associated with different sources, and when a time, condition, event, etc., occurs, the corresponding source is used. For example, in certain embodiments, the selected analyte levels are selected from a first source when the hybrid analyte level output tracks the uncompensated analyte levels, and selected from a second source when the hybrid analyte level output tracks the lag-compensated analyte levels. In certain embodiments, the selected analyte levels are selected from a first source when the hybrid analyte level output tracks the uncompensated analyte levels, selected from a second source when the hybrid analyte level output tracks the lag-compensated analyte levels, and selected from a third source when transitioning from the uncompensated analyte levels to the lag-compensated analyte levels. The sources are exemplary and not intended to be limiting.

The methods, devices, and systems may also include other overriding conditions, which cause the methods, devices, and systems to perform in a different manner as specific times.

The hybrid analyte level output may also include weighted combinations of uncompensated analyte levels and the lag-compensated analyte levels. For example, in certain embodiments, the hybrid analyte level output includes weighted combinations of the uncompensated analyte levels and the lag-compensated analyte levels when transitioning from the uncompensated analyte levels to the lag-compensated analyte levels. In certain embodiments, the hybrid analyte level output includes weighted combinations of the uncompensated analyte levels and the lag-compensated analyte levels when transitioning from the lag-compensated analyte levels to the uncompensated analyte levels. Weighted combinations may be used in one or both transitions in different embodiments. Furthermore, in some instances, the weighted combinations may be used for different durations, or at predetermined times, conditions, events, etc., in different embodiments.

The predetermined criteria may also include parameters that define, in certain instances, when the hybrid analyte output level tracks different sources. For example, in certain embodiments, the predetermined criteria includes criteria for tracking the lag-compensated analyte level until the hybrid analyte output level falls below a predetermined threshold. Further, the hybrid analyte output level tracks a lower of the lag-compensated analyte level and the uncompensated analyte level when the hybrid analyte output level falls below the predetermined threshold. In certain embodiments, a smoothing function may be implemented during transitions. For example, in certain embodiment, the predetermined criteria includes criteria for transitioning smoothly from tracking the lower of the lag-compensated analyte level and the uncompensated analyte level to tracking the lag-compensated analyte levels when the hybrid analyte output level rises back above the predetermined threshold. Further, this smooth transitioning may occur during a predetermined "transition-smoothing" time period. In certain embodiments, the predetermined criteria includes criteria for tracking the lower of the lag-compensated analyte level and the uncompensated analyte level when the hybrid analyte output level falls back below the predetermined threshold before a completion of the predetermined transition-smoothing time period.

In certain embodiments, the lag compensation may be performed on the uncompensated analyte levels—e.g., by applying a lag compensation filter—even when the lag-compensated analyte levels are not selected for output. In this way, both the uncompensated analyte levels and the lag-compensated analyte levels are provided and selected between for the hybrid output. For instance, in some embodiments, both the uncompensated analyte levels and the lag-compensated analyte levels are generated, and the appropriate signal presented on a user-interface. In this way, the display of an analyte monitoring device, for example, displays the uncompensated analyte levels when the hybrid output tracks the uncompensated analyte levels, and displays the lag-compensated analyte levels when the hybrid output tracks the lag-compensated analyte levels.

In certain embodiments, the lag compensation filter may be applied to the uncompensated analyte levels to generate the lag-compensated analyte levels only when the hybrid analyte level output tracks the lag-compensated levels.

In certain embodiments, the hybrid analyte level output may be presented to the user via a user interface element on a device. For example, the hybrid analyte level output may be output audibly and/or visually with a speaker and/or display on an analyte monitoring device. For instance, the analyte monitoring device may be a receiver that receives analyte data from an in vivo sensor. While various analytes may be applicable as described above, in certain embodiments, the analyte is glucose or ketone bodies. In some instances, the uncompensated analyte levels may represent glucose levels derived from interstitial fluid of a patient.

In certain embodiments, the method of generating a hybrid analyte level output includes calculating the uncompensated analyte levels based on the received sensor data, wherein the sensor data is raw sensor data from an in vivo analyte sensor.

In some aspects, analyte monitoring devices are provided that generate the hybrid analyte level output. For example, in certain embodiments, the analyte monitoring devices include a processor; and memory operably coupled to the processor, wherein the memory includes instructions stored therein that, when executed by the processor, cause the processor to generate the hybrid analyte level output—e.g., according to the above described methods.

In certain embodiments, the analyte monitoring device includes a user interface to present the hybrid analyte level output. For example, an analyte monitoring device may include a display and/or speakers to visually and/or audibly present the hybrid analyte level output to the user. In certain embodiments, the analyte monitoring device may include electronics that couple to an in vivo analyte sensor and communicate wired or wirelessly to a receiver. In some instances, the analyte monitoring device may also include the in vivo analyte sensor. In certain embodiments, the analyte monitoring device may be a receiver which communicates with an electronic unit that couples to an in vivo sensor and communicates with the receiver.

In some aspects, analyte monitoring systems are provided that generate the hybrid analyte level output. For example, in certain embodiments, an analyte monitoring systems may include an analyte sensor and analyte monitoring device in communication with the analyte sensor. The analyte monitoring device includes a processor, and memory operably coupled to the processor, wherein the memory includes instructions stored therein that, when executed by the processor, cause the processor to generate a hybrid analyte level output—e.g., according to the above described methods.

In certain embodiments, the analyte sensor includes sensor electronics that couple to an in vivo analyte sensor, and may also include the in vivo analyte sensor coupled to the sensor electronics. The analyte monitoring device is a receiver and may include a user interface to present the hybrid analyte level output. For example, an analyte monitoring device may include a display and/or speakers to visually and/or audibly present the hybrid analyte level output to the user.

In some aspects, analyte monitoring systems are provided that include an analyte sensor and analyte monitoring device in communication with the analyte sensor, wherein the analyte sensor includes a processor, and memory operably coupled to the processor, and wherein the analyte monitoring device includes a processor, and memory operably coupled to its processor. For example, the analyte sensor may include sensor electronics, including the memory and processor, that couple to an in vivo analyte sensor, and may also include the in vivo analyte sensor coupled to the sensor electronics. Furthermore, the analyte monitoring device includes a processor, and memory operably coupled to its processor. At least one of the memories include instructions stored therein that, when executed by the at least one of the processors, causes the at least one processors to generate a hybrid analyte level output—e.g., according to the above described methods.

Some or all of the steps of the methods described above may be performed by the analyte sensor; some or all of the steps of the methods described above may be performed by the receiver; and some or all of the steps of the methods described above may be performed in various combinations by the analyte sensor and the receiver.

For example, in one embodiment, for example, the analyte sensor receives sensor data and generates a hybrid analyte level output. The analyte sensor then, for instance, communicates the hybrid analyte level output to the receiver, which may thereafter present the hybrid analyte level output to the user. In one embodiment, for example, the analyte sensor receives the sensor data and communicates it to the receiver. The receiver then receives the sensor data, generates the lag-compensated analyte levels, and then generates the hybrid analyte level output. In one embodiment, for example, the analyte sensor receives the sensor data, generates the lag-compensated analyte levels, and then communicates the uncompensated and lag-compensated signals to the receiver. The receiver then generates the hybrid analyte level output.

In different embodiments, the sensor data from the in vivo sensor may be calibrated or otherwise converted (e.g., with a scaling factor, etc.) at various times to provide the appropriate analyte levels. For example, in certain embodiments, the sensor data received is raw sensor that is later calibrated or otherwise converted (e.g., with a scaling factor, etc.). In other embodiments, the sensor data may already be calibrated or otherwise converted to the appropriate analyte levels (e.g., glucose levels in mg/DL). In certain embodiments, the lag-compensation may be applied to sensor data that is already calibrated, and the lag-compensated signal generated is at the calibrated analyte level. In certain embodiments, the lag-compensation may be applied to sensor data that is raw, and calibration or conversion required at a later time.

Furthermore, in certain embodiments, calibration or conversion to the appropriate levels occurs before the hybrid output analyte level is generated, and thus the hybrid output analyte level is at the calibrated analyte level when generated. Thus, for example, the threshold levels discussed above are relative to the calibrated analyte levels (e.g., glucose levels in mg/DL). In other embodiments, the hybrid output analyte level may be generated from signals that have not been calibrated or converted, and thus the hybrid output analyte level may require further calibration or conversion before being presented on a user interface. Thus, for example, the threshold levels would be relative to the non-calibrated analyte levels.

For example, in certain embodiments where a receiver receives a hybrid output analyte level from an on-body analyte sensor, the hybrid output analyte level is at the appropriate levels for presenting on a user interface of the receiver, for example. In yet other embodiments where a receiver receives a hybrid output analyte level from an on-body analyte sensor, the hybrid output analyte level is not at the appropriate levels for presenting on the user interface of the receiver, and thus is calibrated or otherwise converted by the receiver before being presented on the user interface. These concepts are equally applicable to the methods, devices, and systems described herein.

In some aspects, computer systems are provided that generate the hybrid analyte level output. For example, in certain embodiments, a computer system may include a processor and memory operably coupled to the processor. The memory includes instructions stored therein that, when executed by the processor, cause the processor to generate a hybrid analyte level output—e.g., according to the above described methods. In certain embodiments, the computer system may include a display.

In some aspects, computer-implemented methods of generating a hybrid analyte level output are provided. The computer-implemented methods include receiving sensor data; and generating a hybrid analyte level output including uncompensated analyte levels and lag-compensated analyte levels, wherein the uncompensated analyte levels lag in time with respect to the lag-compensated analyte levels. The hybrid analyte level output tracks between the uncompensated analyte levels and the lag-compensated analyte levels according to predetermined criteria.

The devices and systems described herein may also include a medication delivery device or system, such as an insulin delivery device or system.

It should be understood that techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium (also generally referred to herein as computer-readable storage medium or computer-readable medium) and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric That which is claimed is:

1. A method of generating a hybrid analyte level output, comprising:
    receiving continuous sensor data comprising uncompensated analyte levels received from an in vivo sensor, the uncompensated analyte levels comprising interstitial fluid glucose levels;
    deriving lag-compensated analyte levels from the uncompensated analyte levels using a processor, the lag-compensated analyte levels comprising estimated blood glucose levels; and
    generating the hybrid analyte level output comprised of the uncompensated analyte levels and the lag-compensated analyte levels using the processor, wherein the uncompensated analyte levels lag in time with respect to the lag-compensated analyte levels;
    wherein the hybrid analyte level output tracks between the uncompensated analyte levels and the lag-compensated analyte levels according to predetermined criteria, the predetermined criteria comprising:
        criteria for tracking the uncompensated analyte levels when selected analyte levels are below a predetermined threshold and have been rising for at least a predetermined duration of time; and
        criteria for tracking the lag-compensated analyte levels when the selected analyte levels are not below the predetermined threshold or have not been rising for at least the predetermined duration of time.

2. The method of claim 1, wherein the selected analyte levels comprise at least one selected from the group consisting of most recently derived lag-compensated analyte levels and most recently received uncompensated analyte levels.

3. The method of claim 1, wherein the generating comprises:

transitioning from the uncompensated analyte levels to the lag-compensated analyte levels and wherein the hybrid analyte level output comprises weighted combinations of the uncompensated analyte levels and the lag-compensated analyte levels when transitioning from the uncompensated analyte levels to the lag-compensated analyte levels; and/or transitioning from the lag-compensated analyte levels to the uncompensated analyte levels and wherein the hybrid analyte level output comprises weighted combinations of the uncompensated analyte levels and the lag-compensated analyte levels when transitioning from the lag-compensated analyte levels to the uncompensated analyte levels.

4. The method of claim 1, wherein the predetermined criteria further comprises criteria for tracking the lag-compensated analyte levels until the hybrid analyte level output falls below a second predetermined threshold, wherein the hybrid analyte level output tracks a lower of the lag-compensated analyte level and the uncompensated analyte level when the hybrid analyte level output falls below the second predetermined threshold.

5. The method of claim 1, wherein deriving the lag-compensated analyte levels comprises applying a lag compensation filter to the uncompensated analyte levels.

6. The method of claim 1, comprising audibly or visually outputting the hybrid analyte level output on a user interface.

7. The method of claim 1, comprising:
audibly or visually outputting the lag-compensated analyte levels on a user interface; and
indicating a low analyte level with the user interface when the lag-compensated analyte levels falls below a predetermined low-entering threshold value.

8. The method of claim 7, comprising:
removing the indication of the low analyte level when a predetermined low-exiting threshold value is exceeded by at least one signal selected from the group consisting of the lag-compensated analyte levels, the uncompensated analyte levels, and the hybrid analyte level output.

9. The method of claim 1, wherein the predetermined threshold comprises a glucose value that indicates hypoglycemia.

10. An analyte monitoring device, comprising:
a processor; and
non-transitory memory operably coupled to the processor, the non-transitory memory including instructions stored therein that, when executed by the processor, cause the processor to:
receive continuous sensor data, comprising uncompensated analyte levels received from an in vivo sensor, the uncompensated analyte levels comprising interstitial fluid glucose levels;
derive lag-compensated analyte levels from the uncompensated analyte levels, the lag-compensated analyte levels comprising estimated blood glucose levels; and
generate a hybrid analyte level output comprised of the uncompensated analyte levels and the lag-compensated analyte levels, wherein the uncompensated analyte levels lag in time with respect to the lag-compensated analyte levels;
wherein the hybrid analyte level output tracks between the uncompensated analyte levels and the lag-compensated analyte levels according to predetermined criteria, the predetermined criteria comprising:
criteria for tracking the uncompensated analyte levels when selected analyte levels are below a predetermined threshold and have been rising for at least a predetermined duration of time; and
criteria for tracking the lag-compensated analyte levels when the selected analyte levels are not below the predetermined threshold or have not been rising for at least the predetermined duration of time.

11. The analyte monitoring device of claim 10, wherein the selected analyte levels comprise at least one selected from the group consisting of most recently derived lag-compensated analyte levels and most recently received uncompensated analyte levels.

12. The analyte monitoring device of claim 10, wherein the hybrid analyte level output transitions from:
the uncompensated analyte levels to the lag-compensated analyte levels and comprises weighted combinations of the uncompensated analyte levels and the lag-compensated analyte levels; and/or
the lag-compensated analyte levels to the uncompensated analyte levels and comprises weighted combinations of the uncompensated analyte levels and the lag-compensated analyte levels.

13. The analyte monitoring device of claim 10, wherein the predetermined criteria further comprises criteria for tracking the lag-compensated analyte level until the hybrid analyte level output falls below a second predetermined threshold, wherein the hybrid analyte level output tracks a lower of the lag-compensated analyte level and the uncompensated analyte level when the hybrid analyte level output falls below the second predetermined threshold.

14. The analyte monitoring device of claim 10, wherein a lag compensation filter is applied to the uncompensated analyte levels to derive the lag-compensated analyte levels.

15. The analyte monitoring device of claim 10, further comprising a user interface, wherein the non-transitory memory includes instructions stored therein that, when executed by the processor, cause the processor to audibly or visually output the hybrid analyte level output on the user interface of the analyte monitoring device.

16. An analyte monitoring system, comprising:
an on-body unit, comprising:
a first processor and first non-transitory memory operably coupled to the first processor;
an in vivo sensor operably coupled to the first processor; and
a receiver configured to communicate with the on-body unit, the receiver comprising:
a second processor and second non-transitory memory operably coupled to the second processor, wherein at least one of the first non-transitory memory and second non-transitory memory includes instructions stored therein that, when executed by at least one of the first processor and second processor, cause the at least one first processor and second processor to:
receive continuous sensor data comprising uncompensated analyte levels received from the in vivo sensor, the uncompensated analyte levels comprising interstitial fluid glucose levels;
derive lag-compensated analyte levels from the uncompensated analyte levels, the lag-compensated analyte levels comprising estimated blood glucose levels; and
generate a hybrid analyte level output comprised of uncompensated analyte levels and lag-compensated analyte levels, wherein the uncompensated analyte levels lag in time with respect to the lag-compensated analyte levels;

wherein the hybrid analyte level output tracks between the uncompensated analyte levels and the lag-compensated analyte levels according to predetermined criteria, the predetermined criteria comprising:
- criteria for tracking the uncompensated analyte levels when selected analyte levels are below a predetermined threshold and have been rising for at least a predetermined duration of time; and
- criteria for tracking the lag-compensated analyte levels when the selected analyte levels are not below the predetermined threshold or have not been rising for at least the predetermined duration of time.

17. The analyte monitoring system of claim 16, wherein the selected analyte levels comprise at least one selected from the group consisting of most recently derived lag-compensated analyte levels and most recently received uncompensated analyte levels.

18. The analyte monitoring system of claim 16, wherein the hybrid analyte level output transitions from:
- the uncompensated analyte levels to the lag-compensated analyte levels and comprises weighted combinations of the uncompensated analyte levels and the lag-compensated analyte levels; and/or
- the lag-compensated analyte levels to the lag-compensated analyte levels and comprises weighted combinations of the uncompensated analyte levels and the lag-compensated analyte levels.

19. The analyte monitoring system of claim 16, wherein the predetermined criteria further comprises criteria for tracking the lag-compensated analyte level until the hybrid analyte level output falls below a second predetermined threshold, wherein the hybrid analyte level output tracks a lower of the lag-compensated analyte level and the uncompensated analyte level when the hybrid analyte level output falls below the second predetermined threshold.

20. The analyte monitoring system of claim 16, wherein the predetermined threshold comprises a glucose value that indicates hypoglycemia.

* * * * *